(12) United States Patent
Rock

(10) Patent No.: US 8,172,782 B2
(45) Date of Patent: May 8, 2012

(54) COMPRESSION GARMENTS

(75) Inventor: Moshe Rock, Brookline, MA (US)

(73) Assignee: MMI-IPCO, LLC, Lawrence, MA (US)

( * ) Notice: Subject to any disclaimer, the term of this patent is extended or adjusted under 35 U.S.C. 154(b) by 316 days.

(21) Appl. No.: 12/618,230

(22) Filed: Nov. 13, 2009

(65) Prior Publication Data

US 2010/0130903 A1 May 27, 2010

Related U.S. Application Data

(60) Provisional application No. 61/117,874, filed on Nov. 25, 2008.

(51) Int. Cl.
*A61F 13/00* (2006.01)

(52) U.S. Cl. .................. 602/62; 602/75; 2/69

(58) Field of Classification Search ............. 602/60–65, 602/20, 23, 75; 2/69, 455, 240, 409; 428/77, 428/78
See application file for complete search history.

(56) References Cited

U.S. PATENT DOCUMENTS

| | | | |
|---|---|---|---|
| 2,713,167 A * | 7/1955 | Cowie et al. ............ 2/458 |
| 3,889,494 A | 6/1975 | Patience et al. | |
| 4,065,814 A | 1/1978 | Fox ............ 2/79 |
| 4,086,790 A | 5/1978 | Hanrahan, Jr. et al. ..... 66/178 A |
| 4,502,301 A | 3/1985 | Swallow et al. ............ 66/178 A |
| 5,819,322 A | 10/1998 | Dicker et al. .......... 2/456 |
| 6,053,852 A | 4/2000 | Wilkinson ............ 482/127 |
| 6,151,927 A | 11/2000 | Owens et al. ............ 66/178 R |
| 6,205,591 B1 | 3/2001 | Wheeler et al. ............ 2/227 |
| 6,276,175 B1 | 8/2001 | Browder, Jr. ............ 66/171 |
| 6,371,933 B1 | 4/2002 | Gardon-Mollard ............ 602/62 |
| 6,430,970 B1 | 8/2002 | Gardon-Mollard et al. 66/178 A |
| 6,572,574 B2 | 6/2003 | Gardon-Mollard ............ 602/62 |
| 6,728,973 B1 | 5/2004 | Webley et al. ............ 2/400 |
| 7,144,294 B2 | 12/2006 | Bell et al. ............ 450/20 |
| 7,159,621 B2 | 1/2007 | Shannon ............ 139/422 |
| 2004/0132367 A1 | 7/2004 | Rock ............ 442/76 |
| 2008/0189824 A1 | 8/2008 | Rock et al. ............ 2/69 |

FOREIGN PATENT DOCUMENTS

| FR | 2 879 901 | 6/2006 |
|---|---|---|
| WO | WO 2006/002371 | 1/2006 |
| WO | WO 2007/112494 | 10/2007 |

OTHER PUBLICATIONS

International Preliminary Report on Patentability; PCT/US2009/065103; Mike Crossley; Mar. 8, 2011.
Compression Garment—Wikipedia, the free encyclopedia, http://en.wikipedia.org/wiki/compression_garment, Nov. 1, 2008, 1 page.
Compression Garment Fabric, http://www.beautysurg.com/shop/garment_fabric.html, Nov. 3, 2008, 4 pages.

(Continued)

*Primary Examiner* — Kim M Lewis
(74) *Attorney, Agent, or Firm* — Fish & Richardson P.C.

(57) ABSTRACT

A compression garment includes a plurality of fabric segments having differing elastic properties arranged to provide the garment with regions of differential compression. The fabric segments define an inner surface of the garment. the inner surface includes at least one region of pile or raised fibers for increased thermal insulation.

38 Claims, 21 Drawing Sheets

OTHER PUBLICATIONS

Compression Sportswear—Wikipedia, the free encyclopedia, http://en.wikipedia.org/wiki/compression_sportswear, Nov. 1, 2008, 1 page.
Compression Stockings—Wikipedia, the free encyclopedia, http://en.wikipedia.org/wiki/Compression_stockings, Oct. 23, 2008, 2 pages.
Compression Tights—Wikipedia, the free encyclopedia, http://en.wikipedia.org/wiki/compression_tights, Nov. 1, 2008, 1 page.
Notification of Transmittal of the International Search Report and the Written Opinion of the International Searching Authority, or the Declaration, International Application No. PCT/US2009/065103, Feb. 25, 2010, 12 pages.

* cited by examiner

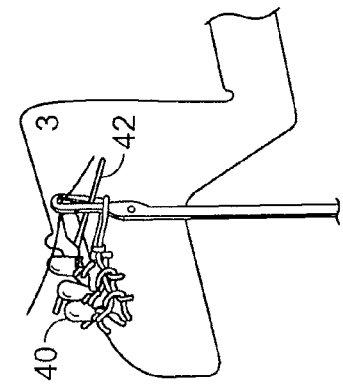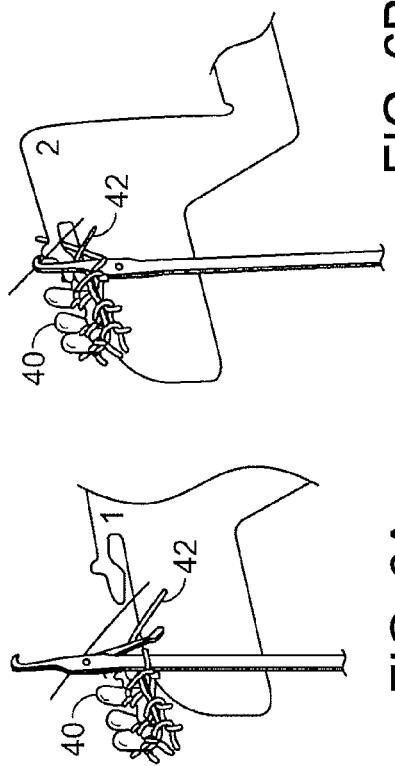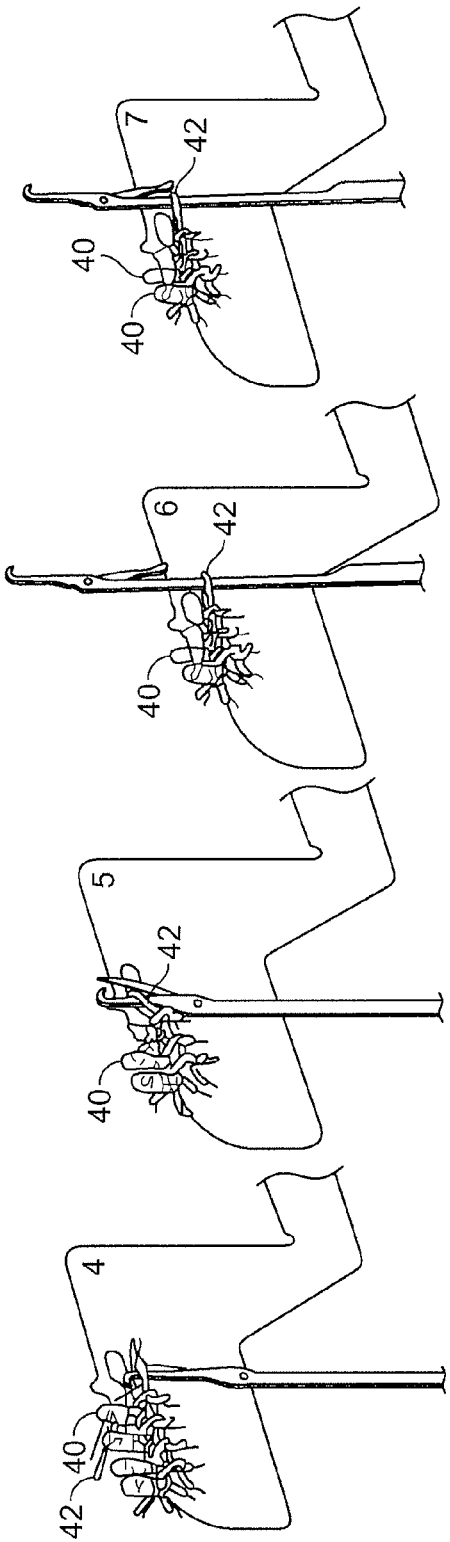
FIG. 6A  FIG. 6B  FIG. 6C  FIG. 6D  FIG. 6E  FIG. 6F  FIG. 6G

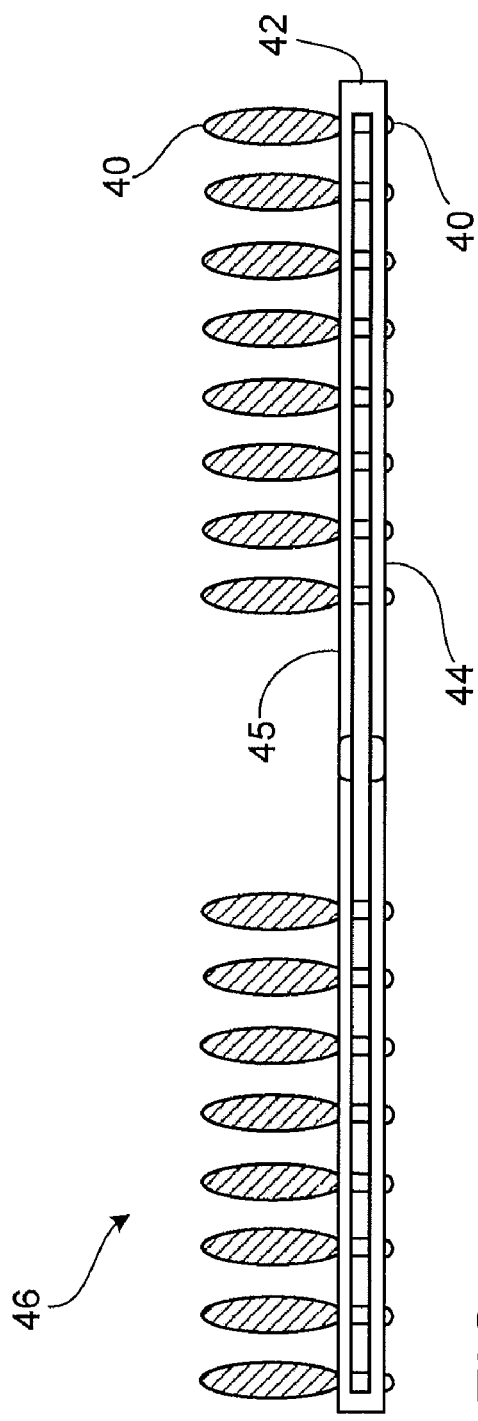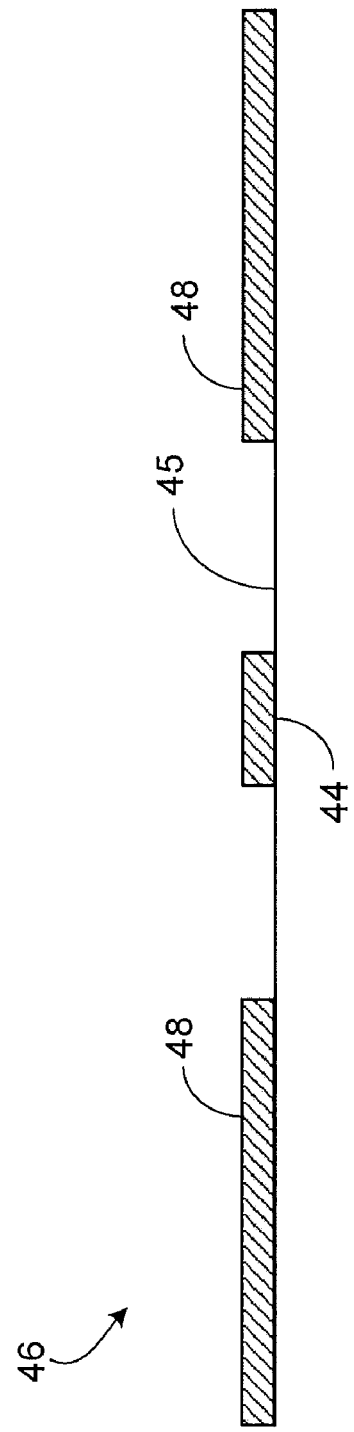

COMPRESSION GARMENTS

CROSS-RELATION OF RELATED APPLICATION

This application claims benefit from U.S. Provisional Patent Application No. 61/117,874, filed on Nov. 25, 2008, the entire contents of which are hereby incorporated by reference.

TECHNICAL FIELD

This disclosure relates to compression garments.

BACKGROUND

Compression garments are articles of clothing that provide support in the form of compressive pressure to regions of a wearer's body. Such garments come in a variety of forms (such as pants, pantyhose, stockings, socks, and sleeves, etc.) and find use in numerous applications including therapeutic and performance enhancing applications. Therapeutic compression garments include, for example, compression stockings, which are often used to support the venous and lymphatic systems of the legs, e.g., for treating poor blood circulation, varicose veins, edema, lymphedema, and deep vein thrombosis. Known compression stockings offer graduated compression where maximum compression is provided at the ankle and decreases along the length of the leg toward the waist. This compression aids in promoting circulation of blood and lymph fluid through the legs and can be beneficial to people with poor blood circulation, people who have to stand for long periods, and/or people who have to sit in one position for extended periods of time (such as when flying long distances).

Another category of compression garment is compression sportswear. Compression sportswear is used, e.g., by athletes, for enhancing muscle performance. Compression sportswear, such as compression sleeves and compression tights, apply compressive pressure to working muscles to promote blood circulation and flow of oxygen to the muscles to help maintain muscle warmth, strength and endurance, and to inhibit cramping, during athletic activities.

Known compression garments typically have fully-fashioned knit construction. In this construction, the fabric is flat, with no raised surface, and provides little or no thermal insulation.

SUMMARY

According to one aspect, a compression garment includes a plurality of circumferential band regions of differential compression arranged in a predetermined pattern corresponding to regions of a user's body. The circumferential band regions define an inner surface of the garment. The inner surface includes at least one region of pile or raised fibers for increased thermal insulation.

Preferred implementations may include one or more of the following additional features and/or steps. In some cases, the inner surface includes a pile surface formed by introducing tufts, loops (e.g., cut or uncut loops), or other erect yarns on all or part of the fabric surface. The plurality of circumferential band regions include a first band region and a second band region. The first band region has a first level of compression and is arranged to coincide with a region of a user's body having a first compression requirement. The second band region has a second level of compression relatively greater than the first level of compression. The second band region is arranged to coincide with another region of the user's body having another compression requirement different from and relatively greater than the first compression requirement. The first band region is arranged to coincide with a joint region of a user's body, and the second band region is arranged to coincide with a muscle region of a user's body. The first band region includes a first wt. % of elastomeric yarn contributing to the first level of compression, and the second band region includes a second wt. % of elastomeric yarn, different from and relatively greater than the first wt. % of elastomeric yarn, contributing the second level of compression. The first band region is seamlessly connected to the second band region. The compression garment may be in the form of a stocking or pants. The second band region is arranged to coincide with a thigh region and/or a hamstring region of a user's body and the first band region is arranged to coincide with a knee region of a user's body. The garment also includes a third band region having a third level of compression different from and relatively greater than the first level of compression, and different from and relatively less than the second level of compression. The first band region has a first wt. % of elastomeric yarn (e.g., about 0.5% to about 10%, e.g., about 4.5%, based on weight of fabric in the first band region) contributing to the first level of compression. The second band region has a second wt. % of elastomeric yarn (e.g., about 8% to about 35%, e.g., about 13.5%, based on weight of fabric in the second band region). The second wt. % is different from and relatively greater than the wt. % of elastomeric yarn, contributing the second level of compression. The third band region has a third wt. % of elastomeric yarn (e.g., about 4% to about 20%, e.g., about 8%, based on weight of fabric in the third band region). The third wt. % is different from and relatively greater than the first wt. % of elastomeric yarn and different from and relatively less than the second wt. % of elastomeric yarn, contributing to the third level of compression. The third band region is seamlessly connected to the first band region and/or to the second band region. The plurality of circumferential band regions are arranged to provide a gradual reduction in compression along a length of the garment. The band regions are configured to provide a gradual reduction in compression along a length of the garment from a first band region arranged to coincide with a thigh region of a user's body toward a second band region arranged to coincide with a lower leg region (e.g., an ankle region) of a user's body below the knee. The band regions are configured to provide a gradual increase in compression along a length of the garment from a first band region arranged to coincide with a thigh region of a user's body toward a second band region arranged to coincide with a lower leg region of a user's body below the knee. The inner surface includes one or more first discrete regions having first pile height and one or more other discrete regions having contrasting pile height different from and relatively greater than the first pile height. The one or more first discrete regions and the one or more other discrete regions are arranged to form a plurality of intersecting channels between a user's body and the garment. The first pile height may be low pile, no pile and combinations thereof, and the contrasting pile height may be high pile, low pile, and combinations thereof. A first one of the band regions defines a first portion of the inner surface having a first pile height, and a second one of the band regions defines a second portion of the inner surface having a second pile height relatively greater than the first pile height. The first one of the band regions has a first predetermined air permeability, and the second one of the band regions has a second predetermined air permeability different from and relatively less than the first predetermined air permeability. A first one of the band regions defines a first portion of the inner surface. The first portion of the inner surface includes one or more first discrete regions having first pile height and one or more other discrete regions having contrasting pile height relatively greater than the first pile height. The one or more first discrete regions and the one or more other discrete regions are arranged to form a plurality of intersecting channels between a user's body and the first one of the band regions. The garment is treated with an antimicrobial agent and/or a wicking agent. In some cases, the garment, e.g., an outer surface of the garment or technical face of fabric forming the garment, may be treated with water repellant and/or abrasion resistant chemical treatment. The inner surface defines a plurality of predetermined, discrete regions of contrasting insulative capacity, including, in one or more first discrete regions, loop yarn having a first pile height, the one or more first discrete regions corresponding to one or more regions of the user's body having first insulative requirements, and, in one or more other discrete regions, loop yarn having another pile height different from and relatively greater than the first pile height, the one or more other discrete regions corresponding to one or more regions of the user's body having other insulative requirements different from and relatively greater than the first insulative requirements. The inner surface has a finish selected from raised sinker loop surface, velour surface, stand alone loop un-napped, and cut loop velour surface. The plurality of circumferential band regions have a woven construction, e.g., a double weave construction. The plurality of circumferential band regions have a knit construction, e.g., a circular knit construction, a plaited circular knit construction, a single face terry loop in plated construction, and/or a warp knit construction. The plurality of circumferential band regions include yarns and/or fibers selected from synthetic yarns and/or fibers, natural yarns and/or fibers, and regenerated yarns and/or fibers. The plurality of circumferential band regions also include elastomeric yarns and/or fibers. The synthetic yarns and/or fibers are selected from polyester yarns and/or fibers, nylon yarns and/or fibers, and acrylic yarns and/or fibers. The natural yarns and/or fibers are selected from cotton yarns and/or fibers and wool yarns and/or fibers. The regenerated yarns and/or fibers include rayon yarns and/or fibers.

In another aspect, a method of forming a compression garment includes combining yarn and/or fibers to form a continuous web that includes a plurality of circumferential band regions of differential compression arranged in a predetermined pattern corresponding to regions of a user's body. The method also includes forming one or more regions of pile or raised fibers in one or more of the band regions.

Preferred implementations may include one or more of the following additional features and/or steps. The plurality of circumferential band regions includes an easy stretch band region having a first level of compression arranged to coincide with a joint region of a user's body, and a compression region having a second level of compression relatively greater than the first level of compression, the compression region being arranged to coincide with a muscle region of a user's body. Combining yarn and/or fibers to form the continuous web includes introducing different wt. % of elastomeric yarn in different ones of the band regions to provide regions of differential compression. The different wt. % of elastomeric yarn include different elastomeric yarn count and/or different number of ends or feeds per length and/or yarns of differing denier. Combining yarn and/or fibers to form the continuous web includes introducing a first wt. % of elastomeric yarn during formation of a first one of the band regions to provide the first one of the band regions with a first level of compression; and introducing a second wt. % of elastomeric yarn, different from and relatively greater than the first wt. % of elastomeric yarn, during formation of a second one of the band regions to provide the second one of the band regions with a second level of compression different from and relatively greater than the first level of compression. The method also includes forming the first one of the band regions in a position on the garment having correlation to a joint region of a user's body; and forming the second one of the band regions in a position on the garment having correlation to a muscle region of a user's body. Combining yarn and/or fibers to form the continuous web further includes introducing a third wt. % of elastomeric yarn, different from and relatively greater than the first wt. % of elastomeric yarn and different from and relatively less than the second wt. % of elastomeric yarn, during formation of a third one of the band regions to provide the third one of the band regions with a third level of compression different from and relatively greater than the first level of compression and different from and relatively less than the second level of compression. The first wt. % is about 0.5% to about 10% (e.g., about 4.5%, based on the weight of fabric in the first band region). The second wt. % is about 8% to about 35% (e.g., about 13.5%, based on weight of fabric in the second band region). The third wt. % is about 4% to about 20% (e.g., about 8%, based on weight of fabric in the third band region). Combining yarn and/or fibers to form the continuous web includes introducing different types of elastomeric yarn in different ones of the band regions thereby to provide regions of differential compression. The different types of elastomeric yarn may include yarns formed of different respective materials. Combining yarn and/or fibers to form the continuous web includes introducing a first type of elastomeric yarn during formation of a first one of the band regions to provide the first one of band regions with a first level of compression; and introducing a second type of elastomeric yarn, different from the first type of elastomeric yarn, during formation of a second one of the band regions to provide the second one of the band regions with a second level of compression different from and relatively greater than the first level of compression. The method also includes forming the first one of the band regions in a position on the garment having correlation to a joint region of a user's body; and forming the second one of the band regions in a position on the garment having correlation to a muscle region of a user's body. Combining yarn and/or fibers includes forming the plurality of circumferential band regions in a shape of a pant leg or a stocking and such that the band regions are arranged to provide a gradual reduction in compression along a length of the garment from a first band region arranged to coincide with a thigh region of a user's body toward a second band region arranged to coincide with a lower leg region of a user's body below the knee. Combining yarn and/or fibers includes forming the continuous web in a shape of a stocking or a pant leg and such that the band regions are arranged to provide a gradual increase in compression along a length of the garment from a first band region arranged to coincide with a thigh region of a user's body toward a second band region arranged to coincide with a lower leg region of a user's body below the knee. Combining yarn and/or fibers includes combining yarn and/or fibers by circular knitting. Combining yarn and/or fibers by circular knitting includes combining yarn and/or fibers by plaiting. The method also includes finishing the one or more regions of pile or raised fibers to form a fleece or velour surface. Forming the one or more regions of pile or raised fibers includes forming loops at the technical back of the continuous web. Combining yarn and/or fibers includes combining yarn and/or fibers by warp knitting. Combining yarn and/or fibers includes combining yarn and/or fibers to form a woven fabric. Combining yarn and/or fibers includes combining yarn and/or fibers to form a fabric with double weave construction. Forming the one or more regions of pile or raised fibers includes forming one or more discrete regions of loop yarn, including forming one or more first discrete regions of loop yarn having first pile height, and forming one or more other discrete regions of loop yarn having contrasting pile height relatively greater than the first pile height. The one or more first discrete regions of loop yarn and the one or more other discrete regions of loop yarn are arranged to form a plurality of intersecting channels. Forming the one or more regions of pile or raised fibers includes, in one or more first discrete regions of the garment, forming loop yarn to a first pile height, the one or more first discrete regions corresponding to one or more regions of a user's body having first insulative requirements, and in one or more other discrete regions of the garment, forming loop yarn to another pile height different from and relatively greater than the first pile height, the one or more other discrete regions corresponding to one or more regions of the user's body having other insulative requirements different form and relatively greater than the first insulative requirements. The method also includes treating the continuous web with an antimicrobial agent and/or a wicking agent. The method also includes treating at least one surface (e.g., at least one of a technical back and technical face) of the continuous web with a durable water repellent.

In another aspect, the invention provides a compression garment that includes a plurality of fabric segments having differing elastic properties arranged to provide the garment with regions of differential compression. The fabric segments define an inner surface of the garment. The inner surface includes at least one region of pile or raised fibers for increased thermal insulation.

Preferred implementations may include one or more of the following additional features and/or steps. In some cases, the inner surface includes a pile surface formed by introducing tufts, loops (e.g., cut or uncut loops), or other erect yarns on all or part of the fabric surface. The fabric segments are arranged to provide a gradual increase or decrease in compression along a length of the garment. The fabric segments have the form of circumferential band regions of differential compression arranged in a predetermined pattern corresponding to regions of a user's body. The plurality of circumferential band regions may include a first band region and a second band region. The first band region has a first level of compression and is arranged to coincide with a region of a user's body having a first compression requirement. The second band region has a second level of compression relatively greater than the first level of compression. The second band region may be arranged to coincide with another region of the user's body having another compression requirement different form and relatively greater than the first compression requirement. In some cases, the first band region may be arranged to coincide with a joint region of a user's body, and the second band region may be arranged to coincide with a muscle region of a user's body. The first band region may have a first wt. % of elastomeric yarn contributing to the first level of compression, and the second band region may include a second wt. % of elastomeric yarn, different from and relatively greater than the wt. % of elastomeric yarn, contributing the second level of compression. In some examples, the first band region is seamlessly connected to the second band region. The compression garment may be in the form of a stocking or pants. The second band region may be arranged to coincide with a thigh region and/or a hamstring region of a user's body and the first band region may be arranged to coincide with a knee region of a user's body. The compression garment may also include a third band region having a third level of compression different from and relatively greater than the second level of compression. In some cases, the first band region includes a first wt. % of elastomeric yarn (e.g., about 0.5% to about 10%, e.g., about 4.5%) contributing to the first level of compression; the second band region includes a second wt. % of elastomeric yarn (e.g., about 4% to about 20%, e.g., about 8%), different from and relatively greater than the first wt. % of elastomeric yarn, contributing the second level of compression; and the third band region includes a third wt. % of elastomeric yarn (e.g., about 8% to about 35%, e.g., about 13.5%), different from and relatively greater than the second wt. % of elastomeric yarn, contributing to the third level of compression. The third band region may be seamlessly connected to the first band region. The third band region may be seamlessly connected to the second band region. The plurality of circumferential band regions may be arranged to provide a gradual reduction in compression along a length of the garment. The compression garment may be in the form of a stocking or pants. The first one of the band regions has a first predetermined air permeability, and the second one of the band regions has a second predetermined air permeability different from and relatively less than the first predetermined air permeability. The band regions may be configured to provide a gradual reduction in compression along a length of the garment from a first band region arranged to coincide with a thigh region of a user's body toward a second band region arranged to coincide with a lower leg region of a user's body below the knee. The band regions may be configured to provide a gradual increase in compression along a length of the garment from a first band region arranged to coincide with a thigh region of a user's body toward a second band region arranged to coincide with a lower leg region of a user's body below the knee. In some embodiments, the fabric segments have the form of complementary shapes which interconnect with each other along the length of the garment. The relative proportions of the fabric segments may change gradually along the length of the garment. The plurality of fabric segments may be connected together via stitching along seams. The plurality of fabric segments may include one or more first fabric segments having a first level of compression; and one or more second fabric segments having a second level of compression relatively greater than the first level of compression. At least one of the one or more first fabric segments and at least one of the one or more second fabric segments have the form of complementary shapes which interconnect with each other within a first region of the fabric garment to provide a gradual increase or decrease in compression along a length of the first region. The relative proportions of the one or more first fabric segments and the one or more second fabric segments gradually change along the length of the first region. The first region exhibits a gradual change in compression pressure along the length of the first region from a first compression pressure of about 5 mmHg to about 30 mmHg near a first end of the first region to a second compression pressure of about 20 mmHg to about 50 mmHg near a second end of the first region. The one or more first fabric segments include a first wt. % of elastomeric yarn (e.g., about 0.5% to about 10%, e.g., about 4.5%) contributing to the first level of compression; and the one or more second fabric segments include a second wt. % of elastomeric yarn (e.g., about 4% to about 20%, e.g., about 8%), different from and relatively greater than the first wt. % of elastomeric yarn, contributing to the second level of compression. The compression garment may also include one or more third fabric segments having a third level of compression different from and relatively greater than the second level of compression.

At least one of the one or more second fabric segments and at least one of the one or more third fabric segments have the form of complementary shapes which interconnect with each other within a second region of the fabric garment to provide a gradual increase or decrease in compression along a length of the second region. The relative proportions of the one or more second fabric segments and the one or more third fabric segments gradually change along the length of the first region. The second region exhibits a gradual change in compression pressure along the length of second region from a first compression pressure of about 20 mmHg to about 50 mmHg near a first end of the second region to a second compression pressure of about 40 mmHg to about 80 mmHg near a second end of the second region. The first region of the fabric garment is arranged to coincide with a thigh region and/or a hamstring region of a user's body, and the second region of the fabric garment is arranged to coincide with lower leg region of a user's body at or below the knee. The one or more first fabric segments include a first wt. % of elastomeric yarn (e.g., 0.5% to about 10%, e.g., about 4.5%) contributing to the first level of compression; the one or more second fabric segments include a second wt. % of elastomeric yarn (e.g., about 4% to about 20%, e.g., about 8%), different from and relatively greater than the first wt. % of elastomeric yarn, contributing to the second level of compression; and the one or more third fabric segments include a third wt. % of elastomeric yarn (e.g., about 8% to about 35%, e.g., about 13.5%), different from and relatively greater than the second wt. % of elastomeric yarn, contributing to the third level of compression. In some cases, the inner surface has a finish selected from: raised sinker loop surface, velour surface, stand alone loop un-napped, and cut loop velour surface. One or more of the fabric segments may have a woven construction (e.g., a double weave construction). One or more of the fabric segments may have a knit construction (e.g., circular knit construction, plaited circular knit construction, single face terry loop in plated construction, and/or warp knit construction). The plurality of fabric segments may include yarns and/or fibers selected from synthetic yarns and/or fibers, natural yarns and/or fibers, and regenerated yarns and/or fibers. The plurality of fabric segments may also include elastomeric yarns and/or fibers. The garment may be treated with an antimicrobial agent and/or a wicking agent. In some cases, the garment, e.g., an outer surface of the garment or technical face of fabric forming the garment, may be treated with water repellant and/or abrasion resistant chemical treatment. In some cases, the inner surface includes one or more first discrete regions having first pile height and one or more other discrete regions having contrasting pile height different from and relatively greater than the first pile height The one or more first discrete regions and the one or more other discrete regions are arranged to form a plurality of intersecting channels between a user's body and the garment.

Another aspect of the invention features a method that includes combining a plurality of fabric segments having differing elastic properties to form a compression garment having regions of differential compression; and forming one or more regions of pile or raised fibers in one or more of the fabric segments.

Preferred implementations may include one or more of the following additional features and/or steps. Methods may include forming the plurality of fabric segments. Forming the plurality of fabric segments may include cutting a plurality of complimentary fabric shapes from respective base fabrics. Cutting the plurality of complimentary fabric shapes may include cutting a first fabric shape from a first base fabric having a first wt. % of elastomeric yarn; and cutting a second fabric shape from a second base fabric having a second wt. % of elastomeric yarn different from and relatively greater than the first wt. %. Combining the plurality of fabric segments may include stitching the complimentary fabric shapes together along seams. Forming the plurality of fabric segments may include combining yarns and/or fibers to form a plurality of circumferential band regions of differential compression. Combining the plurality of fabric segments may include stitching the band regions together along seams. Combining the plurality of fabric segments may include integrally forming the plurality of circumferential band regions such that the band regions are seamlessly connected. Combining yarn and/or fibers may include introducing different wt. % of elastomeric yarn in different ones of the band regions thereby to provide regions of differential compression. Combining the plurality of fabric segments may include arranging the fabric segments to provide a gradual increase in compression along a length of the compression garment.

Other aspects, features, and advantages are in the description, drawings, and claims.

DESCRIPTION OF DRAWINGS

FIGS. 6A-6G are sequential views of a cylinder latch needle in a terry knitting process.

FIG. 7 is a somewhat diagrammatic end section view of a tubular knit fabric article formed during knitting.

FIG. 8 is a somewhat diagrammatic end view of a knit fabric article finished on one surface.

Like reference symbols in the various drawings indicate like elements.

DETAILED DESCRIPTION

Figure 1:
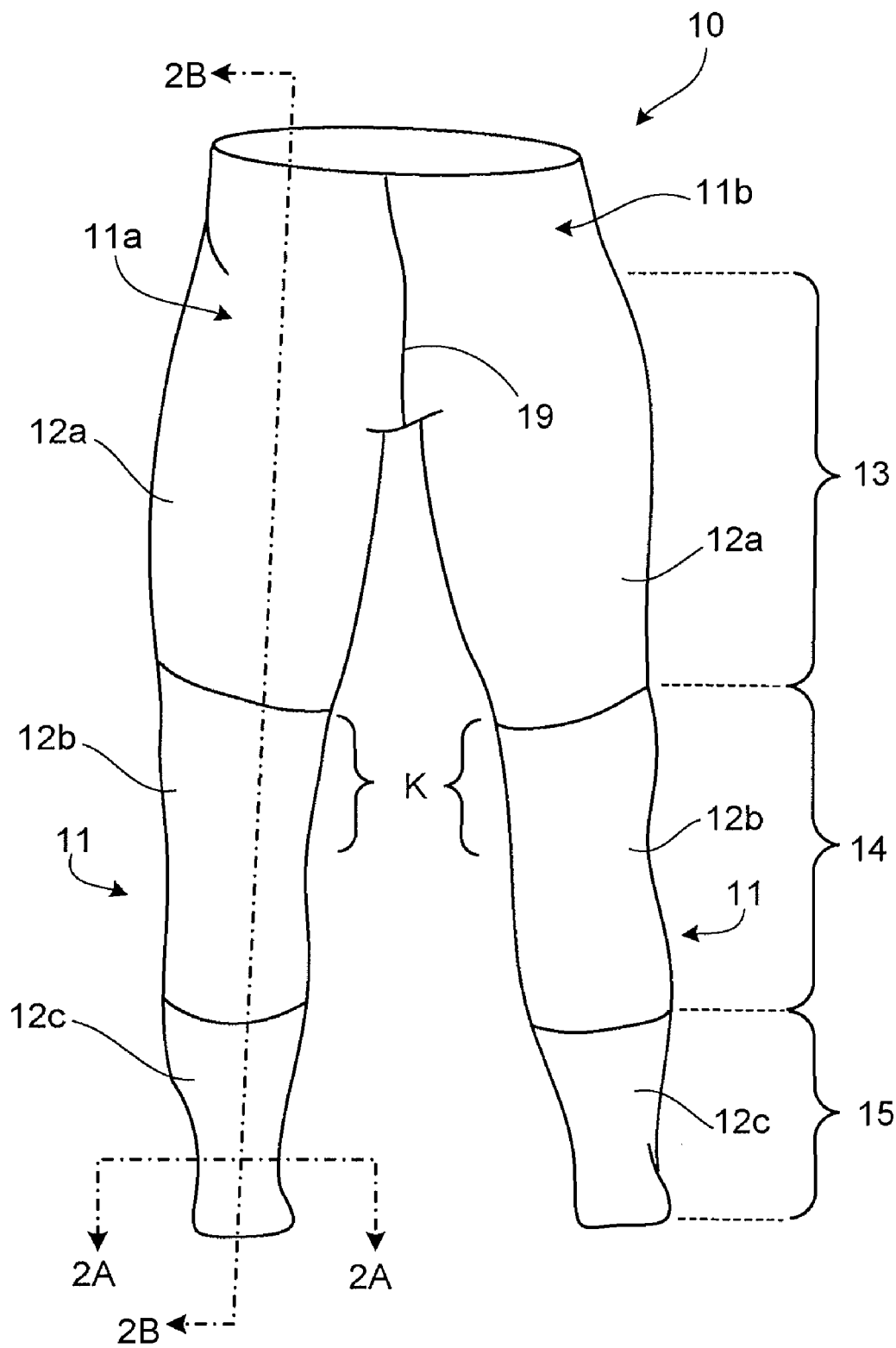
FIG. 1 is a front plan view of a compression garment in the form of pants that includes circumferential band regions of differential compression arranged to provide gradual variation in compression with a maximum compression in ankle regions.

Referring to FIG. 1, a compression garment 10 in the form of pants includes a pair of leg portions 11 each consisting of a plurality of fabric segments, in the form of circumferential band regions 12a, 12b, 12c, of differential compression. The band regions 12a, 12b, 12c are arranged in a predetermined pattern corresponding to region's of a user's body having different compression requirements. The garment 10 of FIG. 1 includes easy stretch band regions 12a (e.g., having a compression pressure of about 5 mmHg to about 30 mmHg), compression band regions 12c (e.g., having a compression pressure of about 40 mmHg to about 80 mmHg), and tight fitting band regions 12b (e.g., having a compression pressure of about 20 mmHg to about 50 mmHg). The easy stretch band regions 12a provide a first level of compression and are constructed to minimize restriction of movement. The compression band regions 12c provide a second level of compression that is different from and relatively greater than the first level of compression. The tight fitting band regions 12b (shown in FIG. 1 in a mid-leg region 14 extending above and below the wearer's knee regions, K) provide a third level of compression that is different from and relatively greater than the first level of compression and that is different from and relatively less than the second level of compression.

As shown in FIG. 1, the band regions 12a, 12b, 12c are arranged to provide a gradual increase in compression along a length the leg portions 11 with less compression in thigh regions 13 and increasingly higher compression in ankle regions 15. This arrangement may help to improve blood circulation from the ankle upward, minimize leg fatigue, reduce the risk of blood clotting and/or enhance the comfort level of the user. Different levels of compression in the band regions 12a, 12b, 12c is achieved by using different elastomeric yarn like Spandex, Lycra, etc., different elastomeric yarn count, different denier elastomeric yarn, and/or different number of ends or feeds per length of elastomeric yarn (e.g., every feed, every other feed, every $n^{th}$ feed, etc.) in different band regions 12a, 12b, 12c.

Figure 2A:
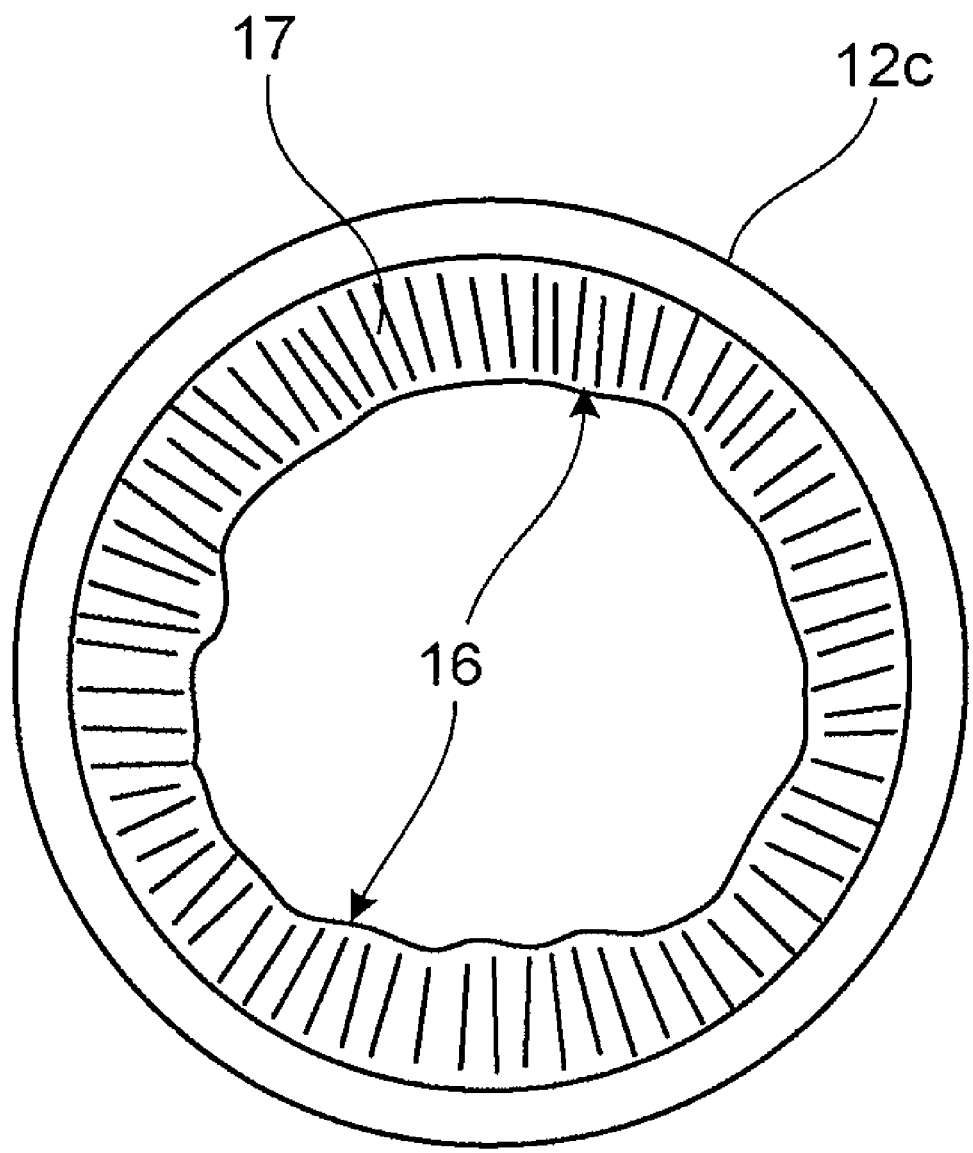
FIG. 2A is a cross-sectional top view of the compression garment of FIG. 1, taken along line 2A-2A.

As illustrated in FIG. 2A, the band regions (band region 12c is shown as an example) extend circumferentially and wholly encompass or surround an associated body region, such as the knee or ankle. In this regard, the individual band regions 12a, 12b, 12c can be formed in seamless construction such that the band regions 12a, 12b, 12c extend entirely circumferentially with no seam along the circumference. As discussed below, the garment fabric can also be formed with seamless construction along its length such that the individual band regions 12a, 12b, 12c are seamlessly interconnected with each other.

Referring again to FIG. 1, individual fabric elements 11a, 11b, each having a seamless construction in both the circumferential and length directions, can be combined, e.g., during a cut-and-sewn process to form the compression garment 10 with only a limited number of seams. As illustrated in FIG. 1, a pair of fabric elements 11a, 11b, each in the form of an individual pant leg having seamless construction, are each partially cut in the compression band region 12c and then joined together by stitching at seam 19. Minimizing the number of seams in the garment 10 can help to contribute to overall comfort and wearability.

Figure 2B:
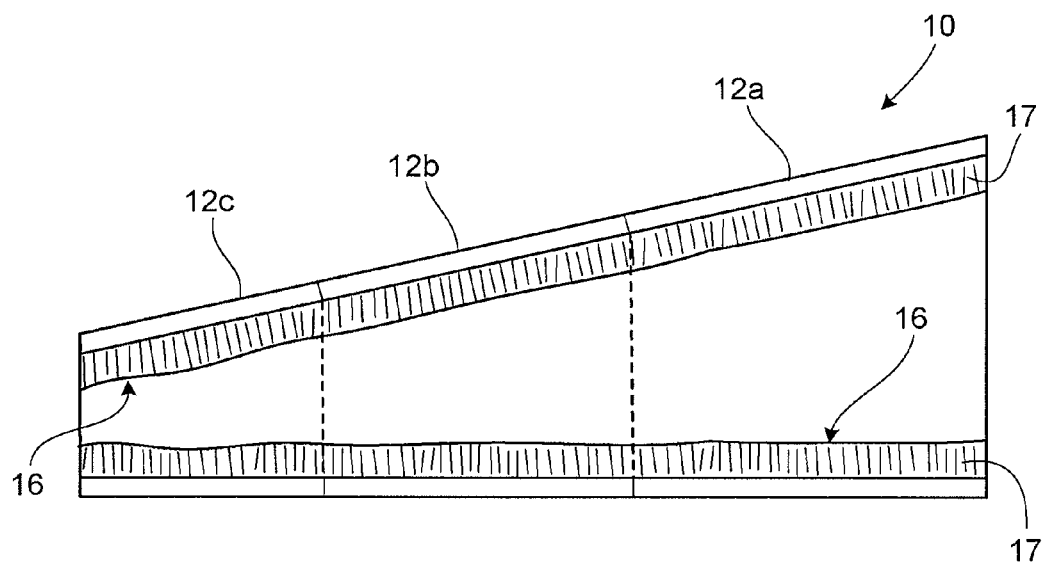
FIG. 2B is a cross-sectional side view of the compression garment of FIG. 1, taken along line 2B-2B.
Figure 2C:
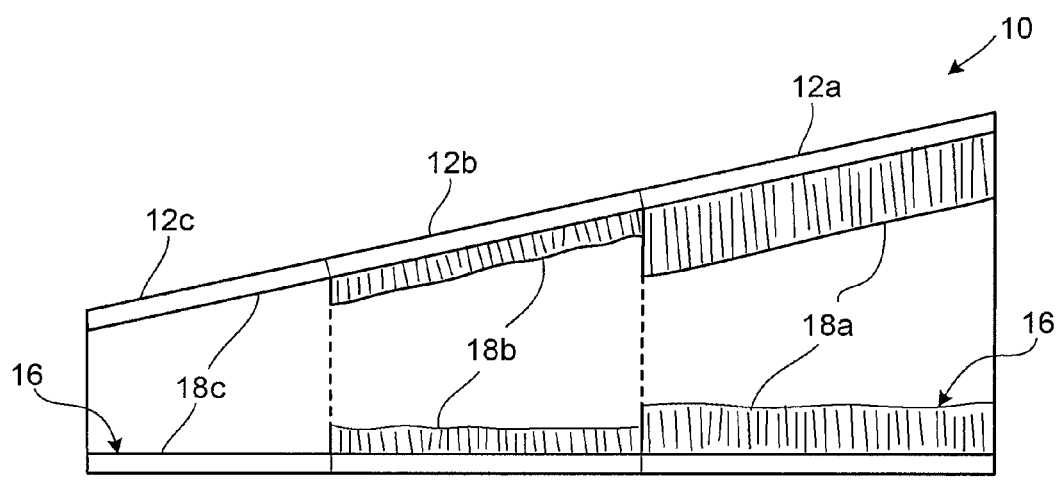
FIG. 2C is a similar cross-sectional side view of an alternative embodiment of a compression garment with regions of contrasting pile height.

As illustrated in FIGS. 2A and 2B, the garment 10 also defines an inner surface 16 having pile or raised fibers 17 for increased thermal insulation. The inner surface 16 faces inwardly towards the user's body when worn. The pile or raised fibers 17 can be formed integrally with the band regions 12a, 12b, 12c, such as by raising selected surfaces of the band regions 12a, 12b, 12c, thus allowing the garment 10 to be formed of a single fabric layer. The inner surface 16 of the garment 10 can be finished to have a substantially constant pile height. Alternatively, referring to FIG. 2C, the inner surface 16 may include regions pile or raised fiber with contrasting pile height. For example, the pattern of pile or raised fibers may be different at each band region 12a, 12b, 12c, as illustrated in FIG. 2C. In this regard, each band region 12a, 12b, 12c may define one or more regions of pile or raised fibers including regions of relatively high pile 18a (having a pile height of about 2.0 mm to about 6.0 mm, e.g., about 3.5 mm), regions of relatively low pile 18b (having a pile height of about 0.5 mm to about 1.5 mm) and/or regions of no pile 18c (e.g., a 0 mm sinker).

The inner surface 16 can have a terry loop finish (e.g., in circular knit or tricot warp knit construction) or floating yarn (e.g., in double weave construction) or inlay on 2 or 3 end circular knit without raising it.

Figure 3A:
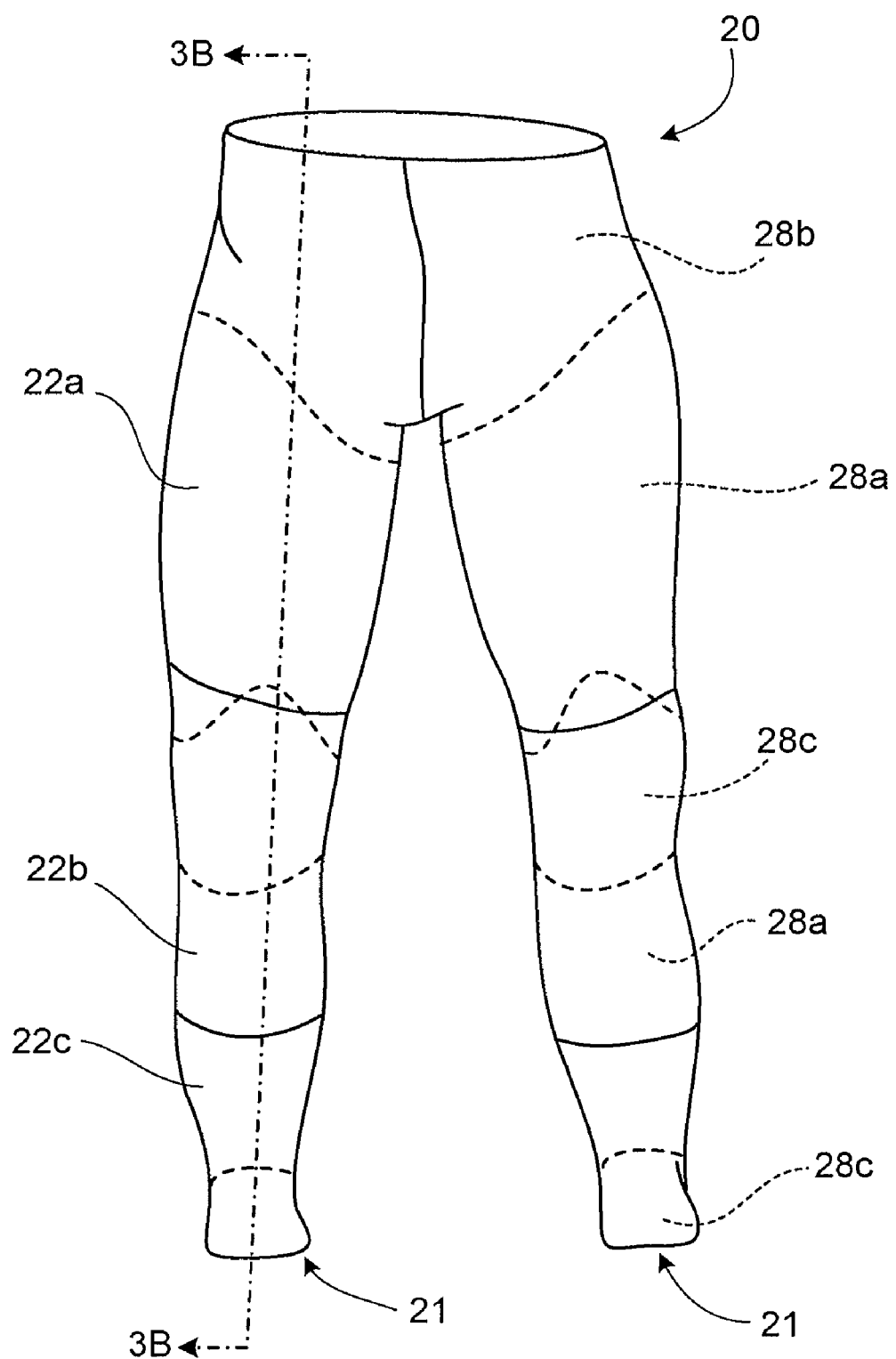
FIG. 3A is a front plan view of another implementation of a compression garment including circumferential band regions of differential compression with integrally formed regions of contrasting pile height arranged by body mapping concepts.
Figure 3B:
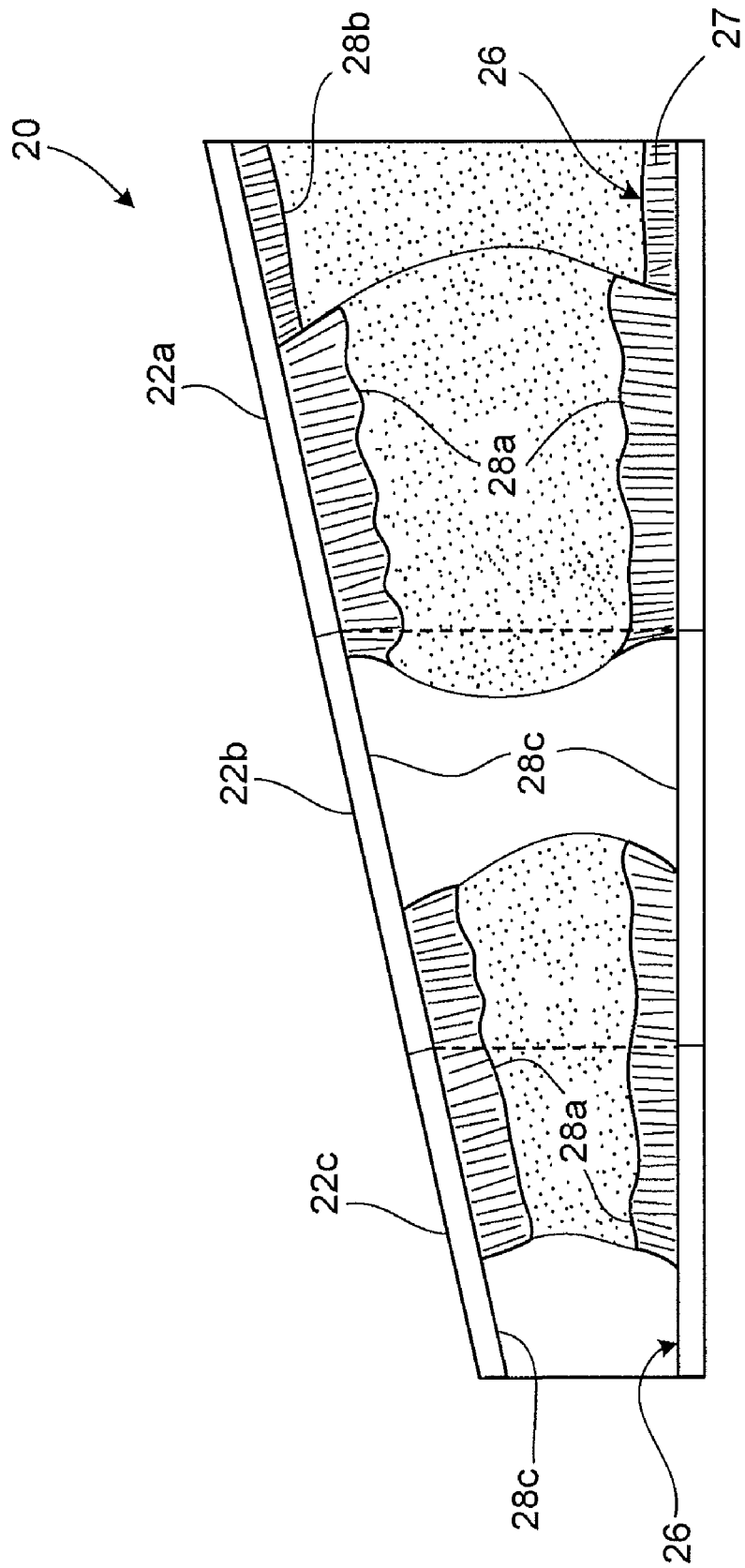
FIG. 3B is a cross-sectional side view of the compression garment of FIG. 3A, taken along line 3B-3B.

In some cases, individual ones of the band regions may include regions of contrasting pile height. For example, FIGS. 3A and 3B illustrate an embodiment in which regions of contrasting pile height are formed selectively across the band regions according to body mapping pattern such that regions of contrasting insulative capacity are arranged in correlation with body regions preferably requiring high insulation, intermediate insulation, and low or no insulation, respectively. In particular, FIGS. 3A and 3B illustrate a compression garment 20 in the form of pants that includes a pair of leg portions 21, each consisting of a plurality of circumferential band regions of differential compression, including easy stretch band regions 22a, compression band regions 22c, and tight fitting band regions 22b. The inner surface 26 of the garment 20 includes regions of relatively high pile 28a arranged to coincide with muscle regions (e.g., thigh and calf regions) of the user's body for relatively high insulative capacity to keep muscles warm. The inner surface 26 also includes regions of relatively low pile 28b in the waist and groin areas of the garment 20 to help reduce overheating while still offering some degree of insulation. The inner surface 26 also includes regions of no pile 28c in ankle and knee regions of the garment 20 for mobility. Additional details regarding the arrangement of regions of pile or raised fibers according to body mapping concepts may be found in U.S. patent application Ser. No. 11/569,041, filed Nov. 13, 2006, the complete disclosure of which is incorporated herein by reference.

Figure 4A:
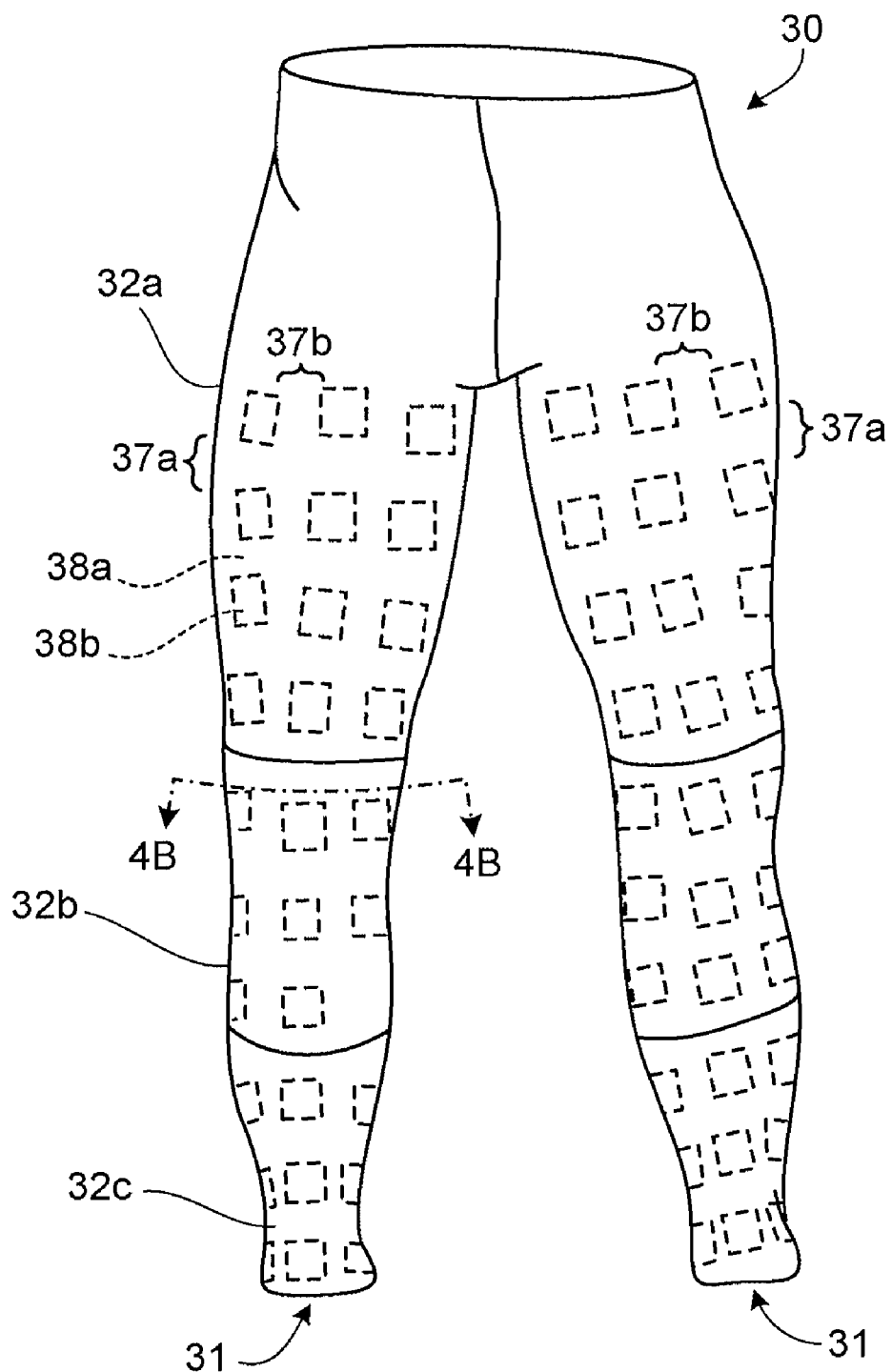
FIG. 4A is a front plan view of another implementation of a compression garment including circumferential band regions of differential compression with integrally formed regions of contrasting pile height arranged to form intersecting channels.
Figure 4B:
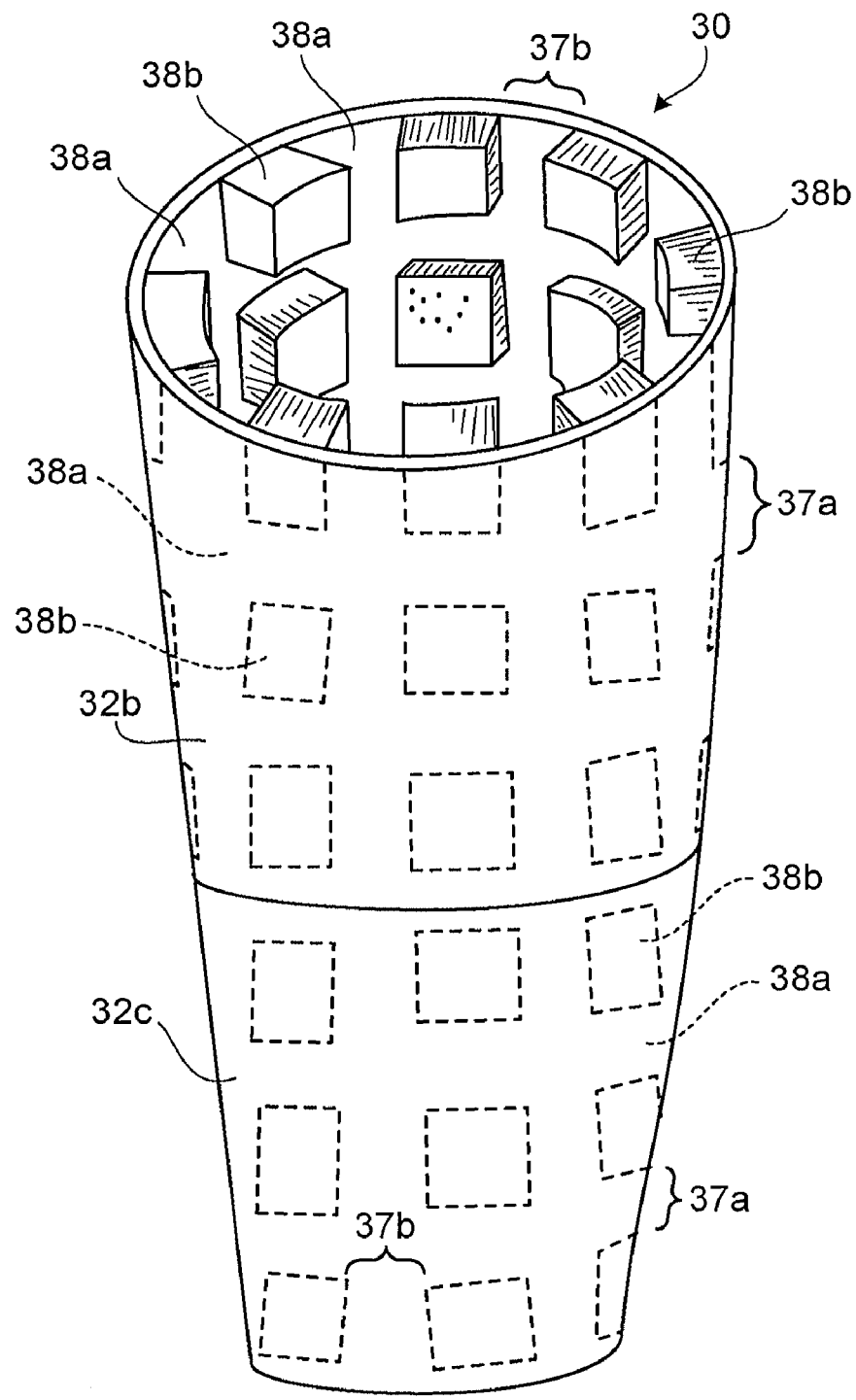
FIG. 4B is a top cross-sectional side perspective view of the compression garment of FIG. 4A, taken along line 4B-4B.
Figure 5:
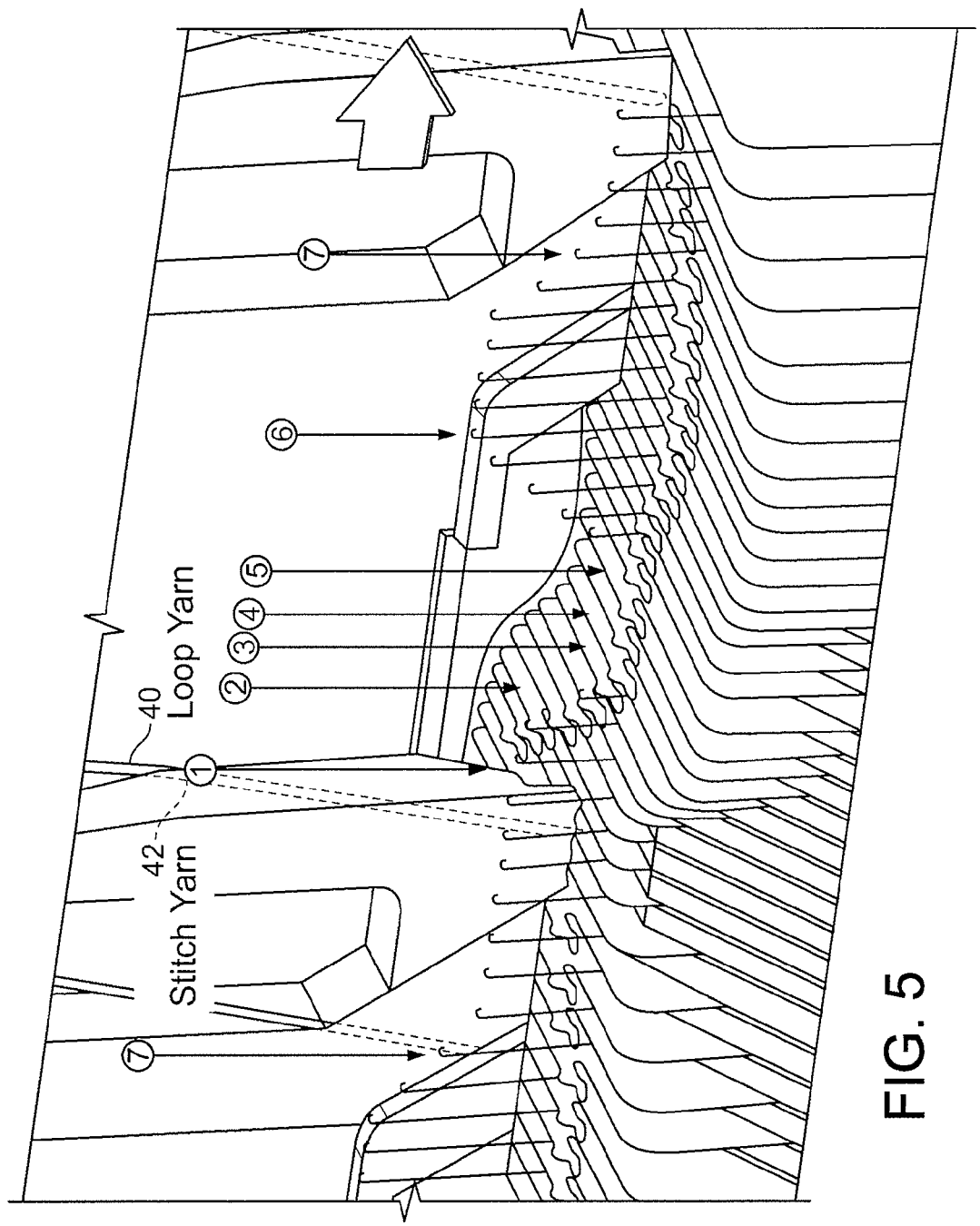
FIG. 5 is a perspective view of a segment of a circular knitting machine.

The inner surfaces of the band regions can also include other patterns of pile or raised fiber. For example, FIGS. 4A and 4B illustrate an embodiment in which channels are constructed within a pile or raised fiber surface. In particular, FIGS. 4A and 4B illustrate a compression garment 30 in the form of pants that includes a pair of leg portions 31, each consisting of a plurality of circumferential band regions of differential compression, including easy stretch band regions 32a, compression band regions 32c, and tight fitting band regions 32b. The band regions 32a, 32b, 32c can have horizontal channels 37a and vertical channels 37b as shown in FIG. 4B. The channel construction within the pile or raised fiber surface 36 provides a thermal insulation layer while allowing for air circulation within the channels 37a and 37b. The channels can be formed by arranging first regions 38a having a first pile height (e.g., low or no pile) between other regions 38b having a second pile height (e.g., low pile or high pile) different from and relatively greater than the first pile height. Additional details regarding channel construction may be found in U.S. Pat. No. 6,927,182, issued Aug. 9, 2005, the complete disclosure of which is incorporated herein by reference.

The fabric used to form the compression garments can be produced by any procedure suitable for creating regions of pile or raised fiber. Examples of suitable procedures include electronic needle and/or sinker selection, tubular circular or terry loop knit construction, e.g., by regular plaiting or reverse plaiting, warp knit construction, and woven construction, e.g., double weave construction. Any suitable yarn or fibers may be employed in forming the fabric. Examples of suitable yarn or fibers include synthetic yarn or fibers formed, e.g., of polyester, nylon, or acrylic; natural yarn or fibers formed, e.g., of cotton or wool; and regenerate yarn or fibers, such as rayon.

In one example, a pattern of circumferential bands of contrasting compression is knitted on a circular knitting machine to form a single layer fabric body with sinker terry loop construction. Elements of the single layer fabric body are then assembled (e.g., during a cut-and-sew process) to form a compression garment. The patterns of the fabric elements are engineered to cover substantial portions of a user's body, each element typically having multiple regions of differential compression seamlessly interconnected with each other to minimize or avoid the cut-and-sew process.

Referring to FIGS. 5 and 6A-6G, a fabric body is formed (in a continuous web) by joining stitch yarn 42 and loop yarn 40 in a terry knitting process. Referring to FIG. 7, in the terry knitting process, the stitch yarn 42 forms the technical face 44 of the resulting fabric body 46 and the loop yarn 40 forms the opposite technical back 45 where it is formed into loops (40, FIG. 6F) extending to overlie the stitch yarn 42. These sinker terry loops can be finished by raising (e.g., napping or brushing) or left in a yarn loop form.

The loop yarn 40 forming the technical back 45 of the knit fabric body 46 can be made of any suitable synthetic or natural material. The cross-section and luster of the fibers or filaments can be varied, e.g., as dictated by requirements of intended end use. The loop yarn can be a spun yarn made by any available spinning technique, or a filament flat or textured yarn made by extrusion. The loop yarn denier is typically between 30 denier to 500 denier. A suitable loop yarn is 70/48 tx polyester yarn.

The stitch yarn 42 forming the technical face 44 of the knit fabric body 46 can also include any suitable type of synthetic or natural material in a spun yarn or a filament yarn. The denier of the stitch yarn 42 is typically between 40 denier to 500 denier. A suitable stitch yarn is 70/68 tx polyester yarn. Compression in the band regions is achieved incorporating elastomeric yarn in the stitch yarn position. As described above, the differing levels of compression in the band regions is achieved by using different elastomeric yarns (e.g., yarns with differing mechanical stretch), different elastomeric yarn count, elastomeric yarns with differing denier, and/or different number of ends or feeds per length of elastomeric yarn (e.g., every feed, every other feed, every $n^{th}$ feed, etc.) in different band regions.

During processing, the fabric elements may be dyed, and finished to form a raised surface. For example, referring to FIG. 8, the fabric body 46 can go through processes of sanding, brushing, napping, etc. to generate a fleece or velour surface 48 in the loop yarn 40 on the technical back 45. Regions of contrasting pile height can be formed by knitting the fabric at different sinker terry loop heights, and/or raised and sheared at different pile/velour heights.

The fabric body 46 can be treated with a wicking agent to improve water management, e.g., to move liquid sweat away from the user's body and towards an outer surface of the garment where it can evaporate. The fabric body 46 can also be treated with an antimicrobial agent to minimize odor. The fabric body 46 can be treated with durable water repellent on the technical face or on both sides (i.e., technical face and technical back).

EXAMPLE

Figure 9:
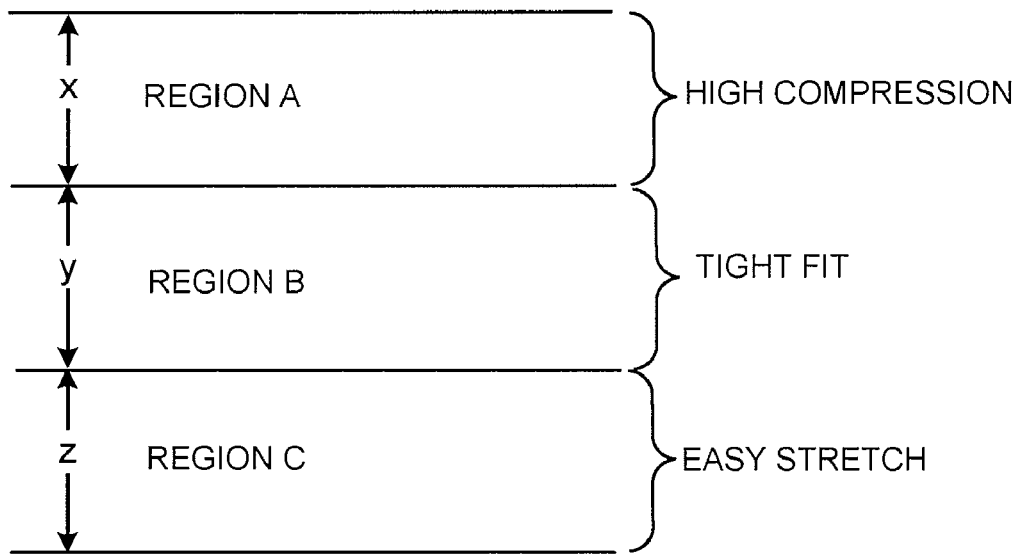
FIG. 9 is a schematic view of knit fabric web including band regions of differential compression.

With reference to FIG. 9, a fabric body including a pattern of circumferential bands of contrasting compression is knitted on a circular knitting machine, plaited sinker terry loop construction, on 24 cut, 26-inch cylinder. The fabric body is made of 70/48 tx polyester yarn on the loop (technical back), and 70/68 tx polyester yarn on the stitch (technical face) and different Lycra count (as follows):

Region A (high compression): 140 denier Lycra on every end, width X=12 inch;

Region B (tight fitting): 70 denier Lycra on every end, width Y=12 inch; and

Region C (easy stretch): 70 denier Lycra on every other end, width Z=12 inch (2 places).

Figure 10:
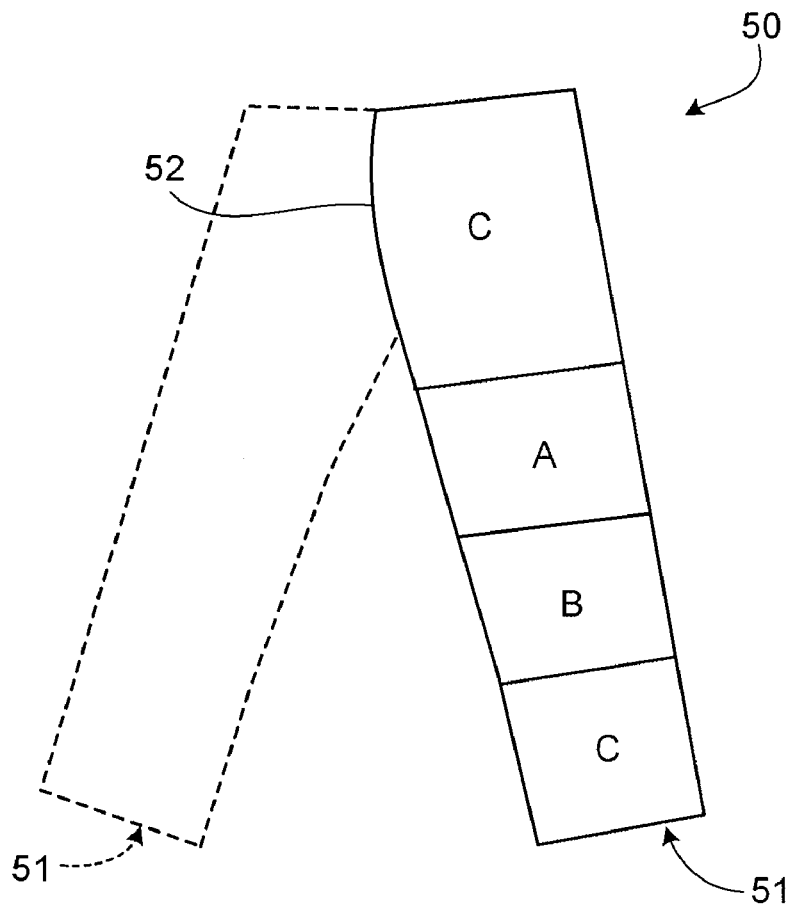
FIG. 10 is a somewhat diagrammatic front plan view of a compression garment formed with the knit fabric web of FIG. 9.

As illustrated in FIG. 10, this will present one repeat along the length of the fabric. In this example, the fabric is dyed and the sinker terry loop surface (technical back) is physically raised to generate fleece or velour. The final fabric will be cut during a cut-and-sew operation to make a long tight leg 51. As illustrated in FIG. 10, a pair of such legs are then joined together (e.g., by stitching at seam 52) to form a compression garment.

OTHER EMBODIMENTS

While certain embodiments have been described above, other embodiments are possible.

Figure 11A:
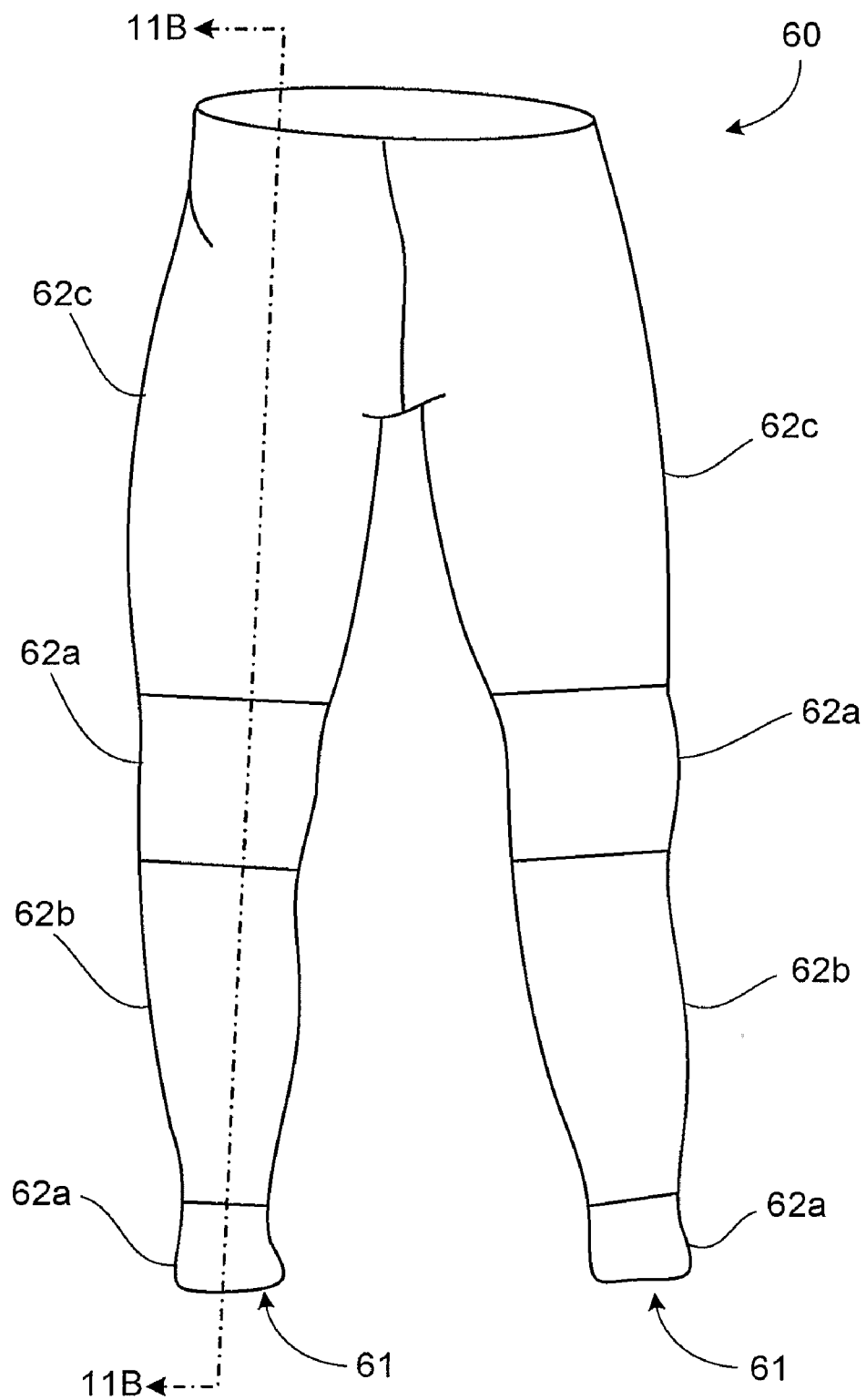
FIG. 11A is a front plan view of another implementation of a compression garment including circumferential band regions of differential compression with compression regions constructed to support muscles, prevent excess vibration and oscillation, and minimize cramping; with tight fitting regions constructed to maintain muscle warmth; and with easy stretch regions constructed to minimize restriction of joints.

For example, while embodiments of compression garments, in the form of pants, have been described above in which a plurality of band regions of differential compression are arranged to provide a gradual increase in compression along a length of leg portions with less compression in thigh regions and increasing toward higher compression in ankle regions, other arrangements of the band regions are possible. As an example, referring to FIG. 11A, a compression garment 60 in the form of pants includes a pair of leg portions 61, each consisting of a plurality of circumferential band regions 62a, 62b, 62c of differential compression that include compression regions 62c (i.e., regions of relatively high compression) arranged to coincide with muscles regions (e.g., thigh, hamstring, etc.) of a user's body. Having regions of relatively high compression supporting the muscles can help to inhibit (e.g., prevent) excess vibration and oscillation, which consumes energy, and thus can help to prevent the user from becoming tired earlier. The risk of muscle cramps is also reduced. The compression garment 60 also includes easy stretch regions 62a, which provide relatively less compression than the compression regions 62c. The easy stretch regions 62a are arranged to coincide with joint regions (e.g., knees, ankles, etc.) of the user's body and are constructed to minimize restriction of movement. The garment 60 can also include tight fitting regions 62b, which provide a level of compression that is different from and relatively greater than the easy stretch regions 62a, and different from and relatively less than the compression regions 62c. The tight fitting regions 62b are arranged to coincide with one or more other regions (e.g., calf regions, shin regions, etc.) of the user's body to help maintain muscle warmth.

Figure 11B:
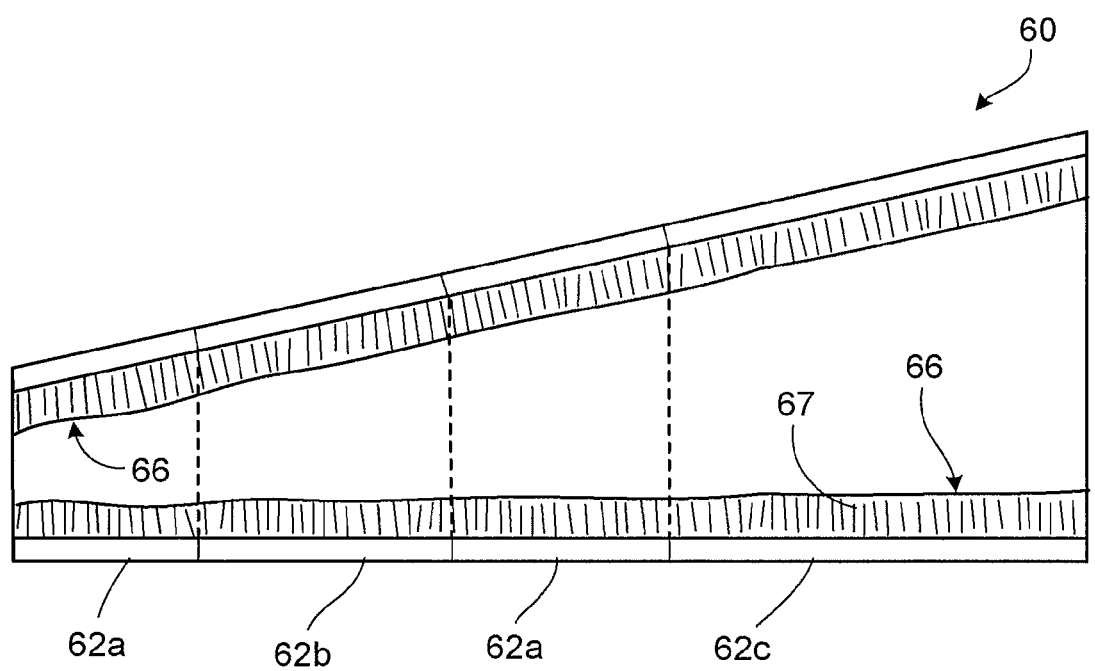
FIG. 11B is a cross-sectional side view of the compression garment of FIG. 11A, taken along line 11B-11B.

As illustrated in FIG. 11B, the garment 60 also defines an inner surface 66 having pile or raised fibers 67, which faces inwardly, towards the user's body, when worn. The pile or raised fibers 67 can be formed integrally with the band regions 62a, 62b, 62c, such as by raising selected surfaces of the band regions 62a, 62b, 62c, thus allowing the garment 60 to be formed of a single fabric layer. The pile or raised surface can go through processes of sanding, brushing, napping, etc. to generate a fleece or velour surface. Having a fleece or velour surface can help to maintain muscle warmth during physical activity, as well as during warm up and cool down exercises. Alternatively, the inner surface 67 can include discrete regions of pile or raised fibers of contrasting pile height, including regions of relatively high pile, regions of relatively low pile, and/or regions of no pile, which may be arranged in a variety of patterns such as described above (e.g., with regard to FIGS. 2C-4B).

Figure 12A:
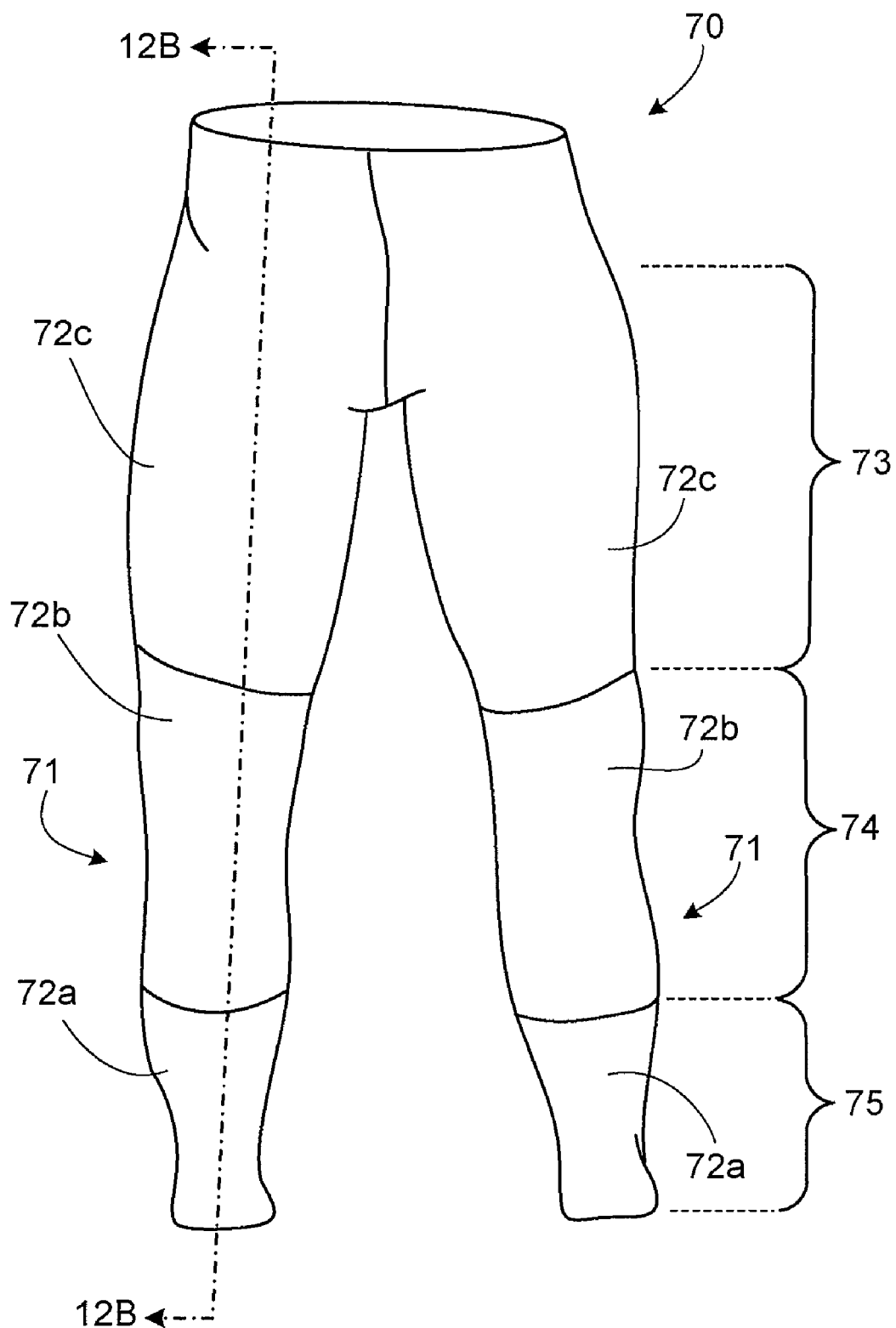
FIG. 12A is a front plan view of another implementation of a compression garment in the form of pants that includes circumferential band regions of differential compression arranged to provide gradual variation in compression with a maximum compression in an upper leg/thigh region.
Figure 12B:
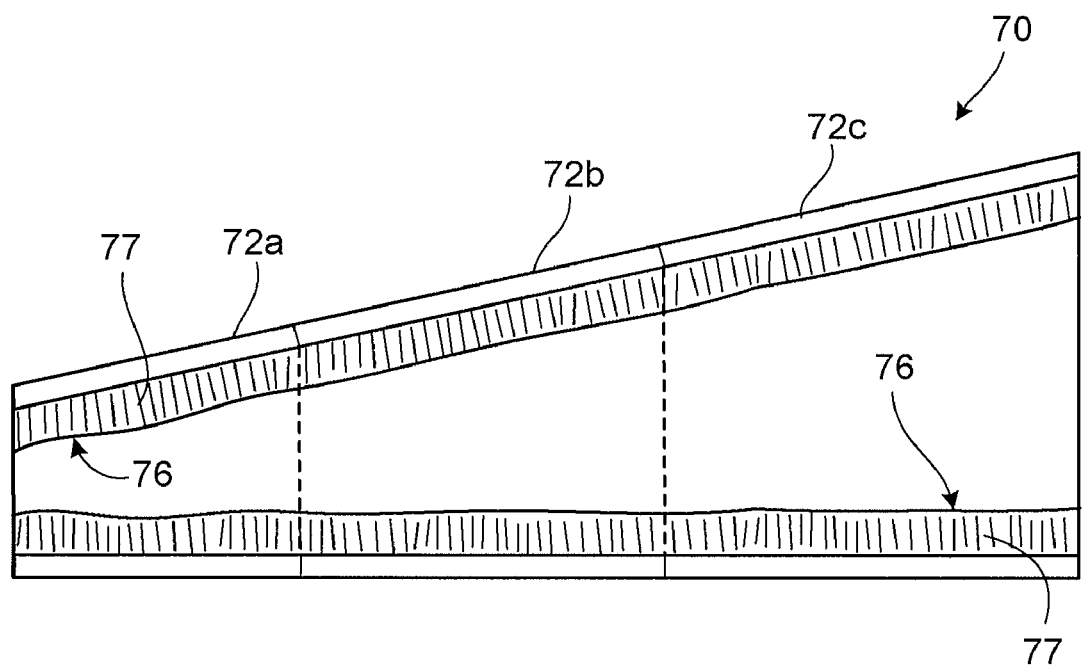
FIG. 12B is a cross-sectional side view of the compression garment of FIG. 12A, taken along line 12B-12B.

As another example, referring to FIGS. 12A and 12B, a compression garment 70 in the form of pants includes a pair of leg portions 71, each consisting of a plurality of circumferential band regions 72a, 72b, 72c of differential compression that are arranged to provide a gradual decrease in compression along a length the leg portions 71 with higher compression in thigh regions 73 and decreasing toward less compression in ankle regions 75. The garment 70 of FIG. 12A includes easy stretch band regions 72a (i.e., regions of relatively low compression) arranged to coincide with ankle regions of a user's body, and compression band regions 72c (i.e., regions of relatively high compression) arranged to coincide with muscle regions (e.g., thigh, hamstring, etc.) of the user's body to support the muscles. The garment may also include tight fitting band regions 72b (shown in FIG. 12A in a mid-leg region 74 extending) providing a level of compression that is between the respective levels of compression provided by the easy stretch and compression regions 72a, 72c, arranged to contribute to muscle warmth.

As illustrated in FIG. 12B, the garment 70 also defines an inner surface 76 having pile or raised fibers 77, which faces inwardly, towards the user's body, when worn. The pile or raised fibers 77 can be formed integrally with the band regions 72a, 72b, 72c, such as by raising selected surfaces of the band regions 72a, 72b, 72c, thus allowing the garment 70 to be formed of a single fabric layer. Alternatively, the inner surface 76 can include discrete regions of pile or raised fibers of contrasting pile height, including regions of relatively high pile, regions of relatively low pile, and/or regions of no pile, which may be arranged in a variety of patterns such as described above (e.g., with regard to FIGS. 2C-4B).

Figure 13A:
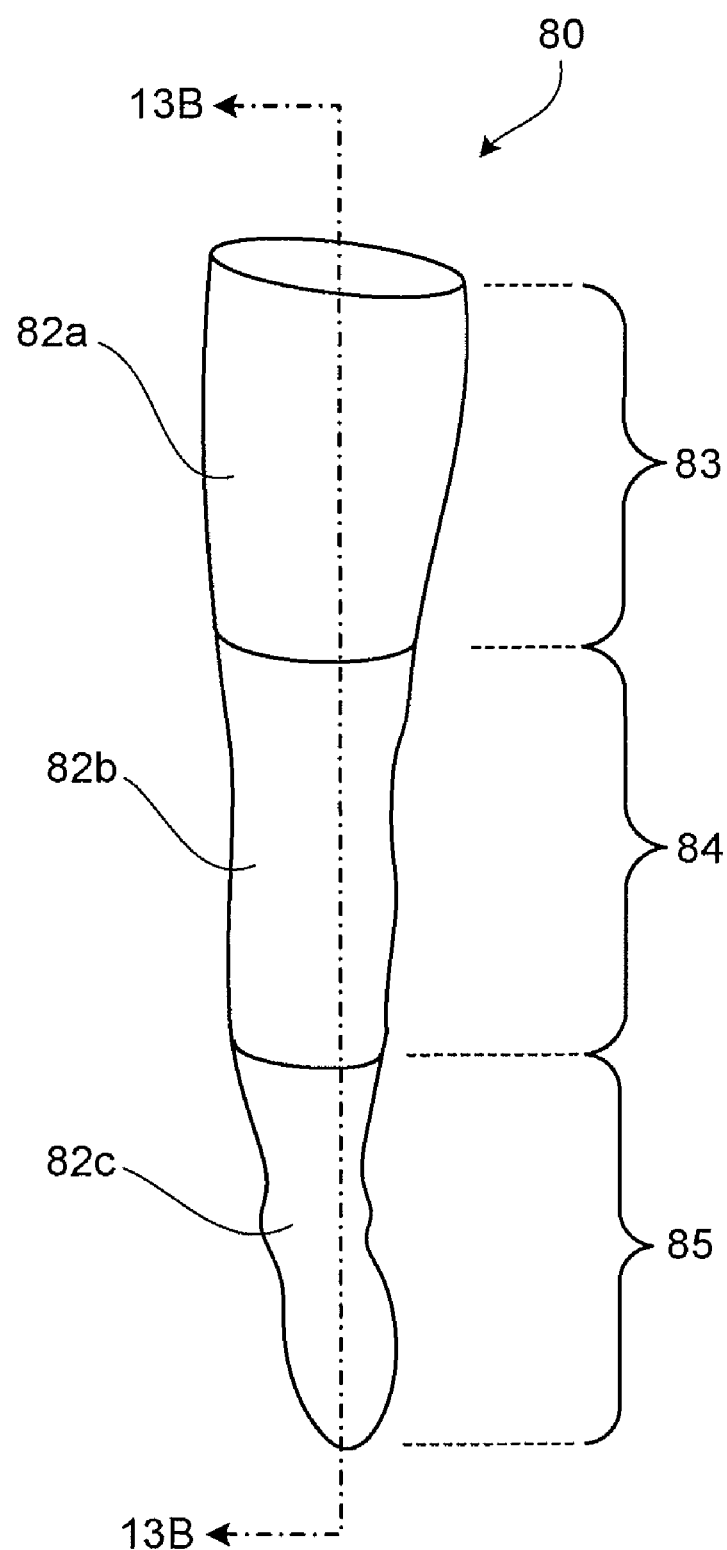
FIG. 13A is a front plan view of another implementation of a compression garment in the form of a stocking that includes circumferential band regions of differential compression arranged to provide gradual variation in compression with a maximum compression in an ankle region.
Figure 13B:
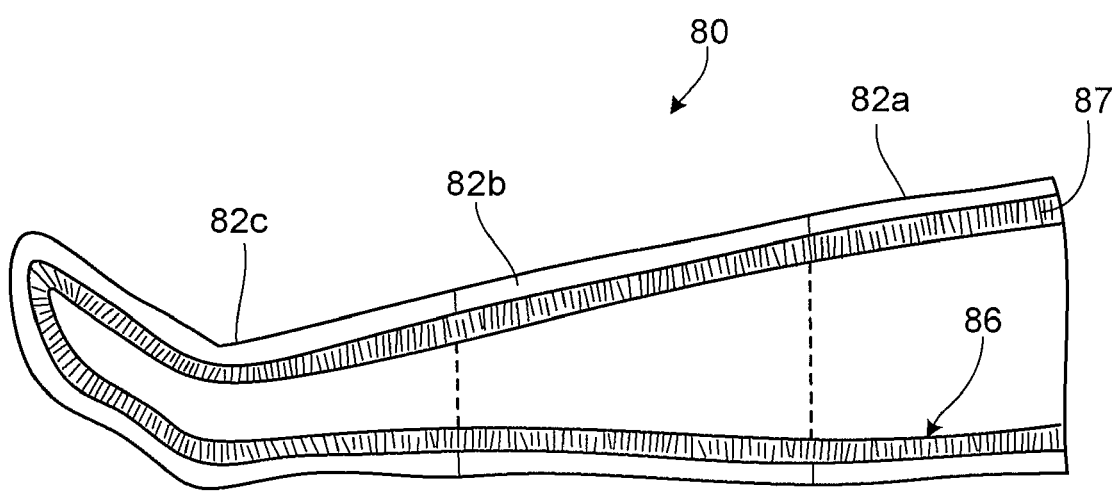
FIG. 13B is a cross-sectional side view of the compression garment of FIG. 13A, taken along line 13B-13B.

The compression garments may also take other forms, other than pants. For example, FIGS. 13A and 13B illustrate a compression garment in the form of a stocking 80. In the illustrated example, the stocking 80 includes a plurality of circumferential band regions 82a, 82b, 82c of differential compression arranged to provide a gradual increase in compression along its length with less compression in a thigh region 83 (i.e., a region of the garment arranged to coincide with a user's thigh) and increasing toward higher compression in an ankle and foot region 85 (i.e., a region of the garment arranged to coincide with a user's ankle and foot). The stocking 80 of FIG. 13A includes easy stretch band region 82a, compression band region 82c, and tight fitting band region 82b. The easy stretch band region 82a provides a first level of compression and are constructed to minimize restriction of movement. The compression band region 82c provides a second level of compression that is different from and relatively greater than the first level of compression. The tight fitting band region 82b provides a third level of compression relatively greater than the first level of compression and relatively less than the second level of compression.

As illustrated in FIG. 13B, the stocking 80 also defines an inner surface 86 having pile or raised fibers 87, which faces inwardly, towards the user's body, when worn. The pile or raised fibers 87 can be formed integrally with the band regions 82a, 82b, 82c, such as by raising selected surfaces of the band regions 82a, 82b, 82c, thus allowing the stocking 80 to be formed of a single fabric layer. Alternatively, the inner surface 86 can include discrete regions of pile or raised fibers of contrasting pile height, including regions of relatively high pile, regions of relatively low pile and/or regions of no pile, which may be arranged in a variety of patterns such as described above.

Furthermore, although embodiments have been described in which a plurality of fabric segments (e.g., band regions) of differential compression are integrally formed with each other without seams, in other embodiments individual band regions, or groups of band regions, can be sewn together, e.g., by stitching along seam, to form a fabric garment.

Figure 14:
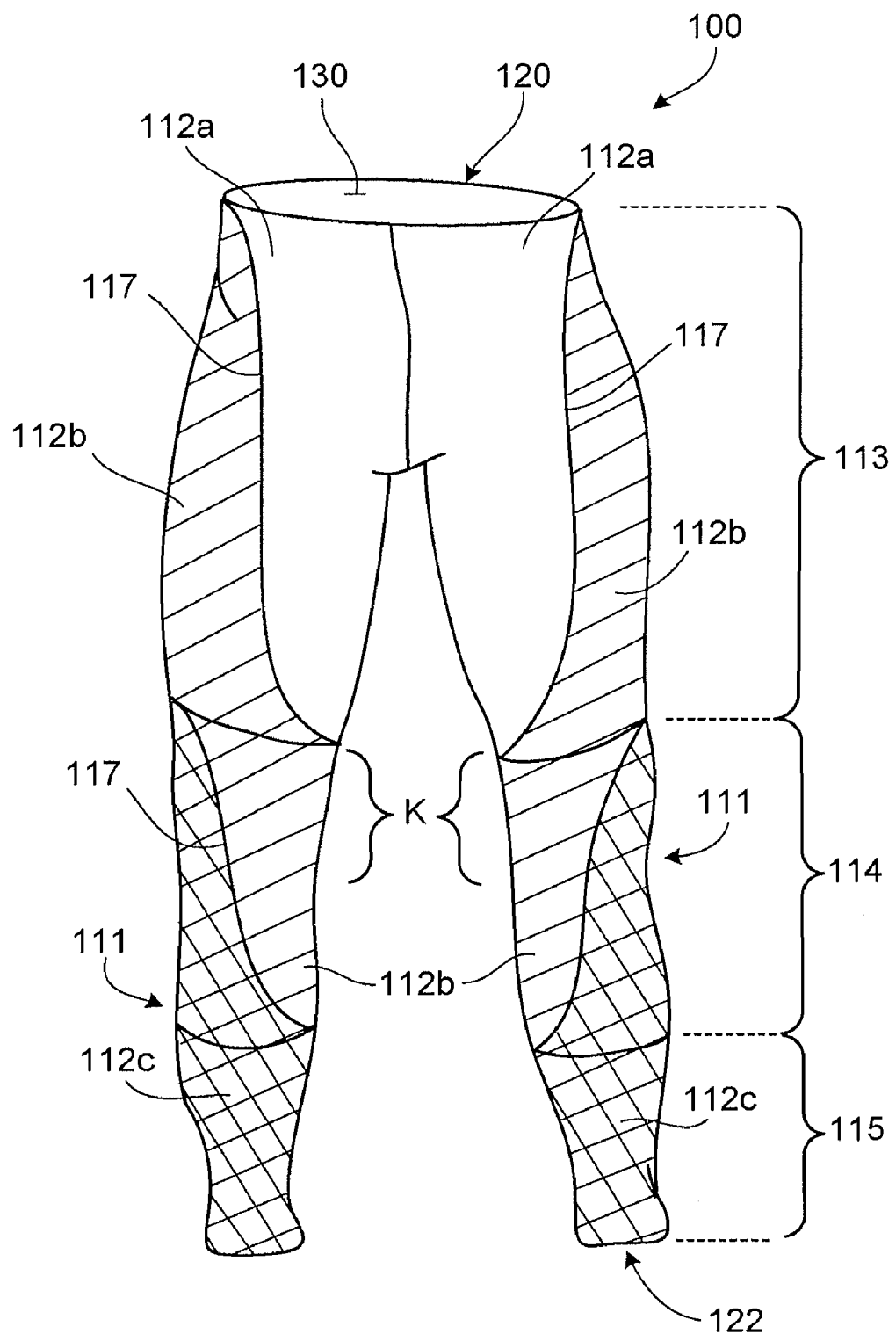
FIG. 14 is a front plan view of a compression garment in the form of pants that includes multiple fabric segments of differential compression having complementary shapes that are arranged to provide gradual variation in compression with a maximum compression in ankle regions.

In a further example, referring to FIG. 14, a compression garment 100 in the form of pants includes a pair of leg portions 111 each consisting of multiple fabric segments 112a, 112b, 112c having contrasting compression characteristics. The multiple fabric segments 112a, 112b, 112c are formed in complementary shapes which interconnect with each other along a length of the leg portions 111 to provide a gradual increase in compression from the waist 120 toward the ankles 122.

The fabric segments 112a, 112b, 112c include easy stretch fabric segments 112a having a first level of compression and are constructed to minimize restriction of movement; tight fitting fabric segments 112b having a second level of compression that is different from and relatively greater than the first level of compression; and compression fabric segments 112c having a third level of compression that is different from and relatively greater than the second level of compression.

Any suitable yarn or fibers may be employed in forming the fabric segments. Examples of suitable yarn or fibers include synthetic yarn or fibers formed, e.g., of polyester, nylon, or acrylic; natural yarn or fibers formed, e.g., of cotton or wool; and regenerate yarn or fibers, such as rayon. The different levels of compression in the easy stretch, tight fitting, and compression fabric segments 112a, 112b, 112c can be achieved by using different elastomeric yarn like Spandex, Lycra, etc., different elastomeric yarn count, different denier elastomeric yarn, and/or different wt. % elastomeric yarn. For example, the easy stretch fabric segments 112a can include about 0.5 wt. % to about 10 wt. %, e.g., about 4.5 wt. %, elastomeric yarn; the tight fitting fabric segments 112b can include about 4 wt. % to about 20 wt. % elastomeric yarn, e.g., about 8 wt. %, elastomeric yarn; and the compression fabric segments 112c can include about 8 wt. % to about 35 wt. %, e.g., about 13.5 wt. %, elastomeric yarn.

As illustrated in FIG. 14, a thigh region 113 of the garment 100 is predominantly formed of the easy stretch fabric segments 112a near the waist, with tight fitting fabric segments 112b making up only a small portion of the garment at the waist 120. The proportions of the easy stretch and the tight fitting fabric segments 112a, 112b gradually change along a length of the thigh region 113 with the tight fitting fabric segments 112b forming a greater portion of the garment 100 as the thigh region 113 transitions to a mid-leg region 114. As a result, the thigh region 113 exhibits relatively lower compression pressure (e.g., about 5 mmHg to about 30 mmHg) at or near the waist 120 and greater compression pressure (e.g., about 20 mmHg to about 50 mmHg) closer to the knees K.

The tight fitting fabric segments 112b extend into the mid-leg region 114 of the garment 100. At the transition with the thigh portion 113, near the knees K, the mid-leg region 114 is predominantly formed of the tight fitting segments 112b with the compression segments 112c forming only a relatively small portion of the garment 100 at the knees K. These proportions gradually change along a length of the mid-leg portion 114 with the compression fabric segments 112c occupying a greater proportion of the garment 100 near the transition to an ankle region 115. As a result, the mid-leg region 114 exhibits relatively lower compression pressure (e.g., about 20 mmHg to about 50 mmHg) at or near the knees K and greater compression pressure (e.g., about 40 mmHg to about 80 mmHg) at or near the transition to the ankle region 115.

The compression fabric segments 112c extend into the ankle portion 115 of the garment 100. As shown in FIG. 14, the ankle region 115 is predominantly formed by the compression fabric segments 112c. The overlapping/intermingling of the fabric segments 112a, 112b, 112c and the gradual change in the proportions of the fabric segments 112a, 112b, 112c along the length of the garment 100 allows for a gradual increase or decrease in power (e.g., a continuous increase or decrease in power) along the legs 111 and can help to avoid localized large differentials in compression along the length of the legs 111.

The garment 100 defines an inner surface 130 having pile or raised fibers for increased thermal insulation. In this regard, the fabric segments 112a, 112b, 112c can be produced by any procedure suitable for creating a pile or raised fiber surface. Examples of suitable procedures include electronic needle and/or sinker selection, tubular circular or terry loop knit construction, e.g., by regular plaiting or reverse plaiting, warp knit construction, and woven construction, e.g., double weave construction. The pile or raised fibers of the inner surface 130 may have the form of a pattern, such as grid, box etc. selected to generate a channeling effect. Alternatively or additionally, the inner surface 130 may have regions of low loop or no loop, or otherwise remaining unraised, disposed among relative raised regions. The arrangement of the respective regions can be determined according to the principles of body mapping, with regions of low loop or no loop positioned to generally overlie surfaces of the user's body requiring relatively low insulation and raised regions being positioned to overlie surfaces of a user's body that require relatively more insulation.

The compression garment can be engineered through the cut-and-sew process to achieve the gradual compression. For example, the individual fabric segments can be cut into predefined shapes and then assembled together (e.g., by stitching along seams 117) in a predetermined pattern via a sewing process to achieve the desired compression.

Figure 15:
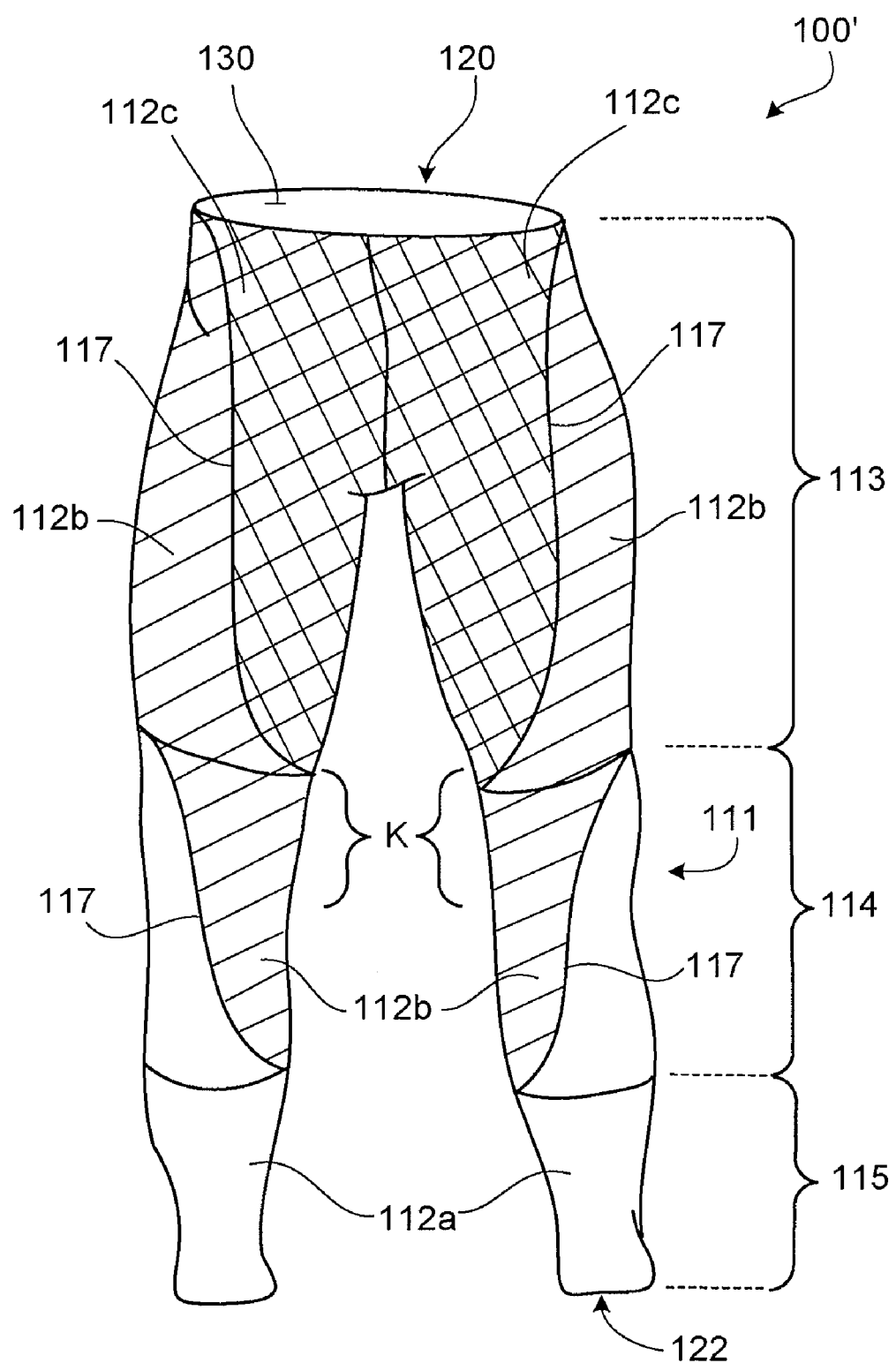
FIG. 15 is a front plan view of a compression garment in the form of pants that includes multiple fabric segments of differential compression having complementary shapes that are arranged to provide gradual variation in compression with a maximum compression in an upper leg/thigh region.

Other arrangements are also possible. For example, FIG. 15 illustrates an alternative configuration of a compression garment 100' in the form of pants in which the easy stretch, tight fitting, and compression fabric segments 112a, 112b, 112c are arranged to achieve a gradual decrease in compression along a length of leg portions 111.

In some cases, the fabric segments may also have contrasting wind resistance.

While examples of garments covering lower body portions (e.g., legs) have been describe above, in some embodiments the garments can, alternatively or additionally, be configured to cover upper body portions (e.g., arms). For example, in some embodiments the compression garments can include a sleeve for covering a wearer's arm.

Figure 16:
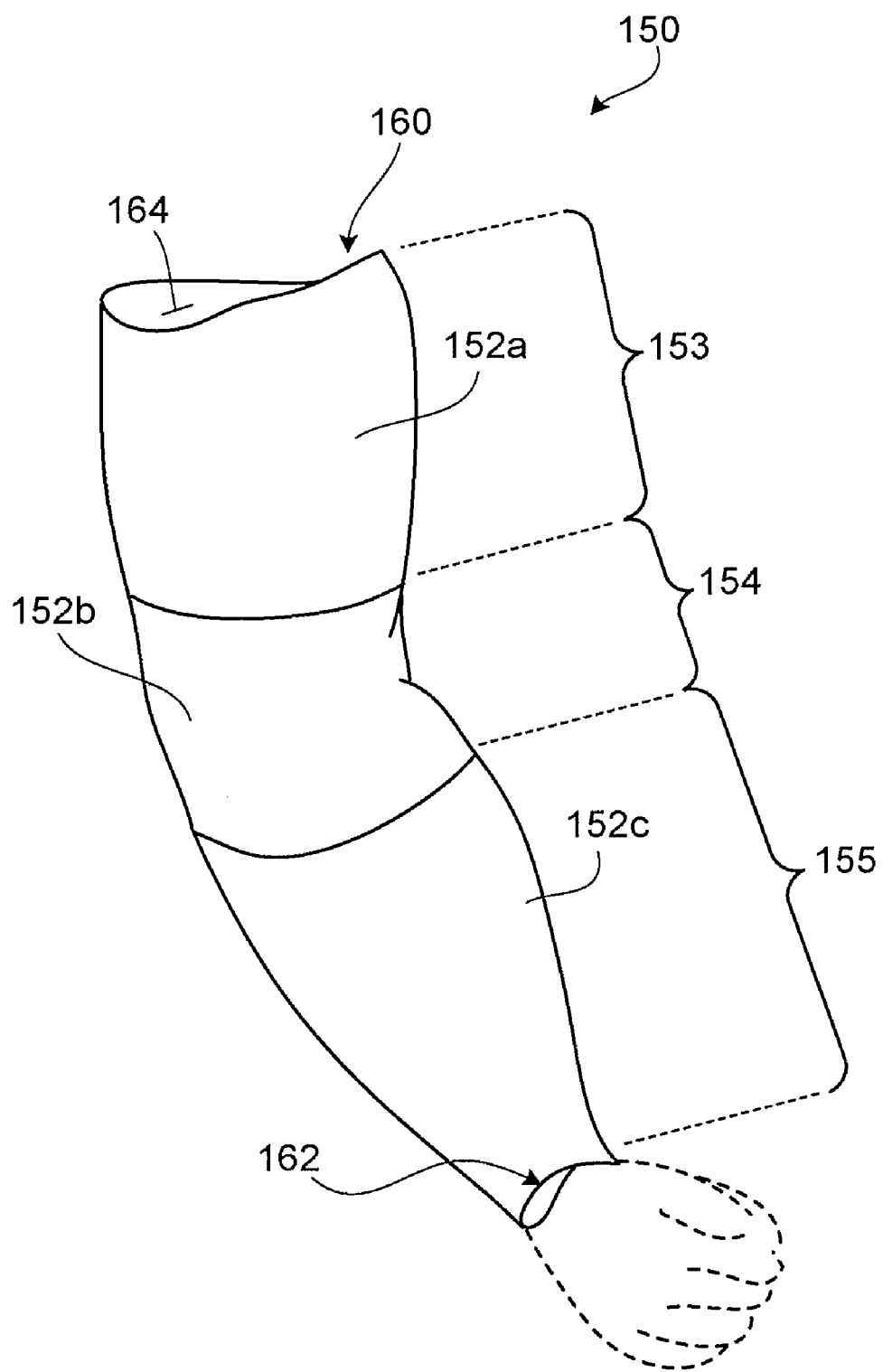
FIG. 16 is a perspective view of a compression garment in the form of a sleeve that includes circumferential band regions of differential compression.

FIG. 16 illustrates a compression garment in the form of a sleeve 150. The sleeve consists of multiple fabric segments, in this case circumferential band regions 152a, 152b, 152c, having contrasting compression characteristics. The sleeve 150 includes an easy stretch band region 152a (shown in a bicep region 153 of the sleeve 150), a tight fitting band region 152b (shown in an elbow region 154 of the sleeve 150), and a compression band region 152c (shown in a bicep region 155 of the sleeve 150). The band regions 152a, 152b, 152c are arranged to provide a gradual decrease in compression from the wrist 162 toward the upper arm 160 of the sleeve 150. The sleeve 150 defines an inner surface 164 having pile or raised fibers for increased thermal insulation. The pile or raised fibers of the inner surface 164 may have the form of a pattern, such as grid, box etc. selected to generate a channeling effect. Alternatively or additionally, the inner surface 164 may include pile or raised fiber regions of contrasting height arranged according to the principles of body mapping.

Figure 17:
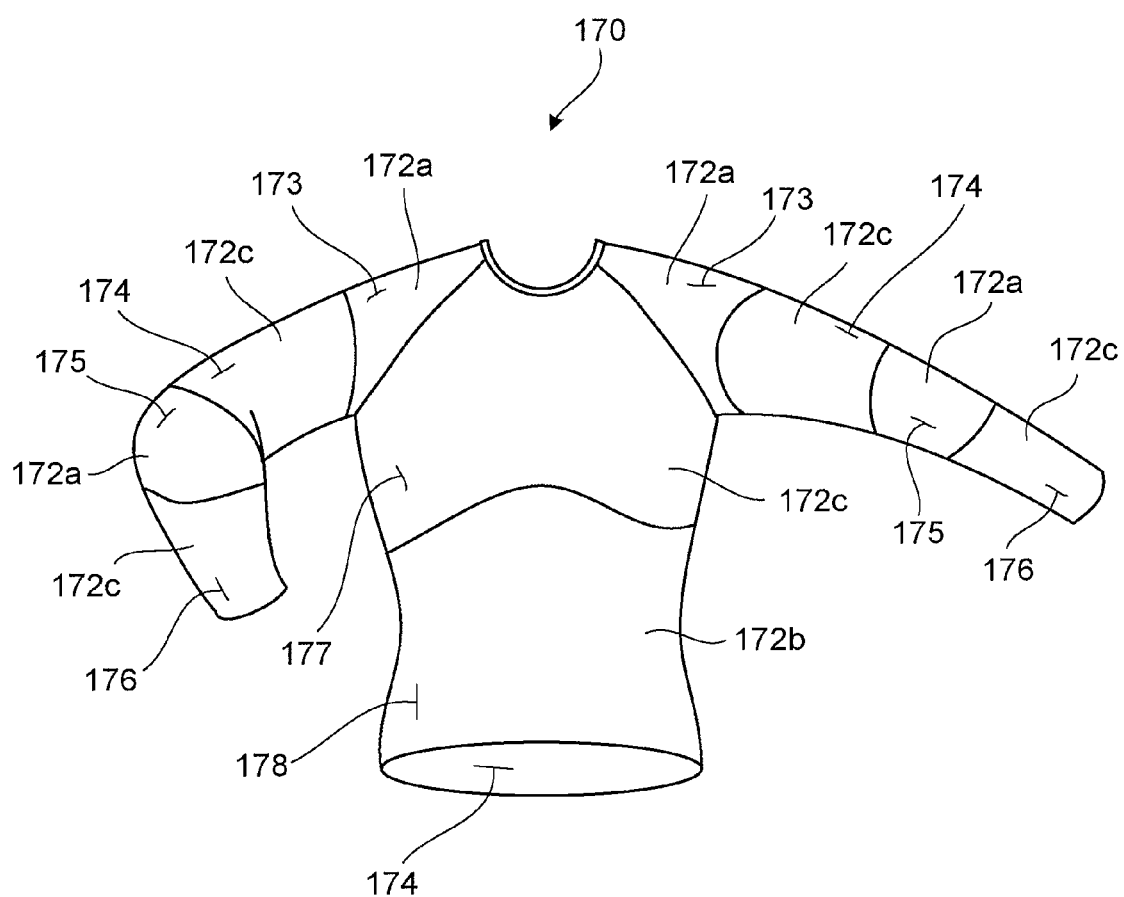
FIG. 17 is a front plan view of a compression garment in the form of a shirt that includes multiple fabric segments having differing elastic properties arranged to provide the shirt with regions of differential compression.

In another example, FIG. 17 illustrates an upper body compression garment in the form of a shirt 170. The shirt 170 includes multiple fabric segments 172a, 172b, 172c having contrasting compression characteristics. The fabric segments 172a, 172b, 172c include easy stretch fabric segments 172a having a first level of compression and constructed to minimize restriction of movement; tight fitting fabric segments 172b having a second level of compression that is different from and relatively greater than the first level of compression; and compression fabric segments 172c having a third level of compression that is different from and relatively greater than the second level of compression. The easy stretch fabric segments 172a are arranged to coincide with joint regions (e.g., elbows 175, shoulders 173, etc.) of the user's body and are constructed to minimize restriction of movement. The compression fabric segments 172c are arranged to coincide with muscle regions (e.g., chest 177, biceps 174, triceps, forearms 176, back, etc.) for supporting the muscles to inhibit excess vibration and oscillation. The shirt 170 also includes tight fitting fabric segments 172*b* that are arranged to coincide with one or more other regions of the user's body (e.g., waist 178) to help maintain muscle warmth while allowing some flexibility.

The shirt 170 defines an inner surface 174 having pile or raised fibers for increased thermal insulation. The fabric segments 172*a*, 172*b*, 172*c* can be produced by any procedure suitable for creating a pile or raised fiber surface. The pile or raised fibers of the inner surface 174 may have the form of a pattern, such as grid, box etc. selected to generate a channeling effect. Alternatively or additionally, the inner surface 174 of the shirt 170 may include pile or raised fiber regions of contrasting height arranged according to the principles of body mapping.

While examples of garments have been described above with particular reference to the human anatomy, in some embodiments, the garments can be configured for animals, such as horses.

Other details and features combinable with those described herein may be found in the U.S. patent application Ser. No. 10/663,091, filed Sep. 15, 2003, the complete disclosure of which is incorporated herein by reference.

Other embodiments are within the scope of the claims.

What is claimed is:

1. A compression garment comprising:
   a plurality of fabric segments having differing elastic properties arranged to provide the garment with regions of differential compression,
   wherein the fabric segments define an inner surface of the garment, the inner surface including at least one region of pile or raised fibers for increased thermal insulation.

2. The compression garment of claim 1, wherein the fabric segments are arranged to provide a gradual increase or decrease in compression along a length of the garment.

3. The compression garment of claim 1, wherein the fabric segments have the form of circumferential band regions of differential compression arranged in a predetermined pattern corresponding to regions of a user's body.

4. The compression garment of claim 3, wherein the plurality of circumferential band regions comprise:
   a first band region having a first level of compression arranged to coincide with a region of a user's body having a first compression requirement; and
   a second band region having a second level of compression relatively greater than the first level of compression, the second band region being arranged to coincide with another region of the user's body having another compression requirement different form and relatively greater than the first compression requirement.

5. The compression garment of claim 4, wherein the first band region is arranged to coincide with a joint region of a user's body, and wherein the second band region is arranged to coincide with a muscle region of a user's body.

6. The compression garment of claim 4, wherein the first band region comprises a first wt. % of elastomeric yarn contributing to the first level of compression, and wherein the second band region comprises a second wt. % of elastomeric yarn, different from and relatively greater than the wt. % of elastomeric yarn, contributing the second level of compression.

7. The compression garment of claim 4, wherein the first band region is seamlessly connected to the second band region.

8. The compression garment of claim 4, in the form of a stocking or pants wherein the second band region is arranged to coincide with a thigh region and/or a hamstring region of a user's body and the first band region is arranged to coincide with a knee region of a user's body.

9. The compression garment of claim 4, further comprising a third band region having a third level of compression different from and relatively greater than the second level of compression.

10. The compression garment of claim 9, wherein the first band region comprises a first wt. % of elastomeric yarn contributing to the first level of compression; wherein the second band region comprises a second wt. % of elastomeric yarn, different from and relatively greater than the wt. % of elastomeric yarn, contributing the second level of compression; and wherein the third band region comprises a third wt. % of elastomeric yarn, different from and relatively greater than the second wt. % of elastomeric yarn, contributing to the third level of compression.

11. The compression garment of claim 10, wherein the first wt. % is about 0.5% to about 10%, the second wt. % is about 4% to about 20%, and the third wt. % is about 8% to about 35%.

12. The compression garment of claim 4, wherein the plurality of circumferential band regions are arranged to provide a gradual reduction in compression along a length of the garment.

13. The compression garment of claim 4, wherein the first one of the band regions has a first predetermined air permeability, and the second one of the band regions has a second predetermined air permeability different from and relatively less than the first predetermined air permeability.

14. The compression garment of claim 3, in form of a stocking or pants, wherein the band regions are configured to provide a gradual reduction in compression or a gradual increase in compression along a length of the garment from a first band region arranged to coincide with a thigh region of a user's body toward a second band region arranged to coincide with a lower leg region of a user's body below the knee.

15. The compression garment of claim 3, in form of a stocking or pants, wherein the band regions are configured to provide a gradual increase in compression along a length of the garment from a first band region arranged to coincide with a thigh region of a user's body toward a second band region arranged to coincide with a lower leg region of a user's body below the knee.

16. The compression garment of claim 1, wherein the fabric segments have the form of complementary shapes which interconnect with each other along the length of the garment.

17. The compression garment of claim 1, wherein the relative proportions of the fabric segments change gradually along the length of the garment.

18. The compression garment of claim 1, wherein the plurality of fabric segments are connected together via stitching along seams.

19. The compression garment of claim 1, wherein the plurality of fabric segments comprise:
   one or more first fabric segments having a first level of compression; and
   one or more second fabric segments having a second level of compression relatively greater than the first level of compression,
   wherein at least one of the one or more first fabric segments and at least one of the one or more second fabric segments have the form of complementary shapes which interconnect with each other within a first region of the fabric garment to provide a gradual increase or decrease in compression along a length of the first region.

20. The compression garment of claim 19, wherein the relative proportions of the one or more first fabric segments and the one or more second fabric segments gradually change along the length of the first region.

21. The compression garment of claim 19, wherein the one or more first fabric segments comprise a first wt. % of elastomeric yarn contributing to the first level of compression; and wherein the one or more second fabric segments comprise a second wt. % of elastomeric yarn, different from and relatively greater than the first wt. % of elastomeric yarn, contributing to the second level of compression.

22. The compression garment of claim 19, further comprising one or more third fabric segments having a third level of compression different from and relatively greater than the second level of compression.

23. The compression garment of claim 22, wherein the one or more first fabric segments comprise a first wt. % of elastomeric yarn contributing to the first level of compression; the one or more second fabric segments comprise a second wt. % of elastomeric yarn, different from and relatively greater than the first wt. % of elastomeric yarn, contributing to the second level of compression; and the one or more third fabric segments comprise a third wt % of elastomeric yarn, different from and relatively greater than the second wt. % of elastomeric yarn, contributing to the third level of compression.

24. The compression garment of claim 23, wherein the first wt. % is about 0.5% to about 10%, the second wt. % is about 4% to about 20%, and the third wt. % is about 8% to about 35%.

25. The compression garment of claim 1, wherein the fabric segments are seamlessly connected to each other.

26. The compression garment of claim 1, in the form of a pant, a stocking, a sleeve, or a shirt.

27. The compression garment of claim 1, wherein the plurality of fabric segments have a single face plaited construction.

28. The compression garment of claim 1, wherein the inner surface includes one or more first discrete regions having first pile height and one or more other discrete regions having contrasting pile height different from and relatively greater than the first pile height, and wherein the one or more first discrete regions and the one or more other discrete regions are arranged to form a plurality of intersecting channels between a user's body and the garment.

29. A method comprising:
combining a plurality of fabric segments having differing elastic properties to form a compression garment having regions of differential compression; and
forming one or more regions of pile or raised fibers in one or more of the fabric segments.

30. The method of claim 29, further comprising forming the plurality of fabric segments.

31. The method of claim 30, wherein forming the plurality of fabric segments includes:
cutting a plurality of complimentary fabric shapes from respective base fabrics.

32. The method of claim 31, wherein cutting the plurality of complimentary fabric shapes comprises:
cutting a first fabric shape from a first base fabric having a first wt. % of elastomeric yarn; and
cutting a second fabric shape from a second base fabric having a second wt. % of elastomeric yarn different from and relatively greater than the first wt. %.

33. The method of claim 31, wherein combining the plurality of fabric segments comprises stitching the complimentary fabric shapes together along seams.

34. The method of claim 30, wherein forming the plurality of fabric segments comprises:
combining yarns and/or fibers to form a plurality of circumferential band regions of differential compression.

35. The method of claim 34, wherein combining the plurality of fabric segments comprises stitching the band regions together along seams.

36. The method of claim 34, wherein combining the plurality of fabric segments comprises integrally forming the plurality of circumferential band regions such that the band regions are seamlessly connected.

37. The method of claim 34, wherein combining yarn and/or fibers comprises introducing different wt. % of elastomeric yarn in different ones of the band regions thereby to provide regions of differential compression.

38. The method of claim 34, wherein combining the plurality of fabric segments comprises arranging the fabric segments to provide a gradual increase in compression along a length of the compression garment.

* * * * *